(12) United States Patent
Sankai

(10) Patent No.: US 8,945,018 B2
(45) Date of Patent: Feb. 3, 2015

(54) BLOOD FLOW MEASURING APPARATUS AND BRAIN ACTIVITY MEASURING APPARATUS USING THE SAME

(75) Inventor: Yoshiyuki Sankai, Tsukuba (JP)

(73) Assignee: University of Tsukuba, Tsukuba-Shi, Ibaraki (JP)

( * ) Notice: Subject to any disclaimer, the term of this patent is extended or adjusted under 35 U.S.C. 154(b) by 598 days.

(21) Appl. No.: 12/499,309

(22) Filed: Jul. 8, 2009

(65) Prior Publication Data

US 2009/0270745 A1  Oct. 29, 2009

(30) Foreign Application Priority Data

Feb. 14, 2008 (JP) ................................. 2008-033617

(51) Int. Cl.
  *A61B 5/02* (2006.01)
  *A61B 5/026* (2006.01)
  *A61B 5/00* (2006.01)

(52) U.S. Cl.
  CPC ............. *A61B 5/0261* (2013.01); *A61B 5/6814* (2013.01)
  USPC ........... 600/504; 600/507; 600/505; 600/544; 600/545

(58) Field of Classification Search
  CPC ...... A61B 5/026; A61B 5/028; A61B 5/0535; A61B 5/022; A61B 5/0476; A61B 5/0482
  USPC .......................... 600/504–507, 544, 545, 324
  See application file for complete search history.

(56) References Cited

U.S. PATENT DOCUMENTS

| | | | |
|---|---|---|---|
| 5,490,506 A | 2/1996 | Takatani et al. | |
| 5,935,062 A | 8/1999 | Messerschmidt et al. | |
| 7,179,279 B2 * | 2/2007 | Radons et al. ................ | 607/108 |
| 2005/0107716 A1 * | 5/2005 | Eaton et al. ................... | 600/544 |

(Continued)

FOREIGN PATENT DOCUMENTS

| | | |
|---|---|---|
| EP | 0 720 013 A2 | 7/1996 |
| GB | 2 228 314 A | 8/1990 |

(Continued)

OTHER PUBLICATIONS

Cooper et al., Design and evaluation of a probe for simultaneous EEG and near-infrared imaging of cortical activation, Mar. 2009, Phys. Med. Biol., vol. 54, pp. 2093-2102.*

(Continued)

*Primary Examiner* — Patricia Mallari
*Assistant Examiner* — Tho Tran
(74) *Attorney, Agent, or Firm* — Ladas & Parry LLP

(57) ABSTRACT

A blood flow measuring apparatus includes a sensor unit including a light emitter configured to emit light onto a measurement area and a light receiver configured to receive the light transmitted through the measurement area; at least one more light receiver configured to receive the light transmitted through the measurement area; and a control part configured to measure a blood flow state of the measurement area according to signals outputted by the light receivers. The light emitted by the light emitter is received by the light receivers arranged at different distances from the light emitter and the light receivers output the signals responsive to the received light. The control part measures the blood flow state of the measurement area by performing an arithmetic process to cancel a component of oxygen saturation in the blood, said component being included in the signals outputted by the light receivers.

11 Claims, 21 Drawing Sheets

(56) References Cited

U.S. PATENT DOCUMENTS

| | | |
|---|---|---|
| 2005/0277819 A1* | 12/2005 | Kiani et al. .................. 600/324 |
| 2007/0083097 A1 | 4/2007 | Fujiwara et al. |
| 2007/0100218 A1* | 5/2007 | Sweitzer et al. ............. 600/323 |
| 2008/0265145 A1 | 10/2008 | Uchida |
| 2009/0116167 A1* | 5/2009 | Stevenson et al. ......... 361/306.1 |
| 2010/0280571 A1* | 11/2010 | Sloan ............................. 607/45 |

FOREIGN PATENT DOCUMENTS

| | | |
|---|---|---|
| JP | 2002-345787 A | 12/2002 |
| JP | 2003-144401 A | 5/2003 |
| JP | 2003-149137 A | 5/2003 |

OTHER PUBLICATIONS

EPO Communication dated Apr. 11, 2014; Appln. No. 09 165 079.6-1660.

Stéphane Perrey; "Non-invasive NIR spectroscopy of human brain function during exercise", Methods: A Companion to Methods in Enzymology, Academic Press Inc., New York, NY, US, vol. 45, No. 4, Aug. 1, 2008, pp. 289-299, XP025399364, ISSN: 1046-2023.

Kevin R. Ward, et al; "Near infrared spectroscopy for evaluation of the trauma patient: a technology review", Resuscitation, Elsevier, IE, vol. 68, No. 1, Jan. 1, 2006, pp. 27-44, XP025066745: ISSN: 0300-9572.

European Search Report: EP 09 16 5079, Oct. 2009.

* cited by examiner (ELAPSED TIME = t1)

(ELAPSED TIME = t2)

(ELAPSED TIME = t3)

BLOOD FLOW MEASURING APPARATUS AND BRAIN ACTIVITY MEASURING APPARATUS USING THE SAME

BACKGROUND OF THE INVENTION

1. Field of the Invention

The present invention generally relates to a blood flow measuring apparatus configured to accurately measure a blood supply state without being influenced by an oxygen saturation concentration of the blood, and to a brain activity measuring apparatus using the blood flow measuring apparatus.

2. Description of the Related Art

As apparatuses to measure a blood flow, for example, there have been brain activity measuring apparatuses, which are used by wearing a probe that forms an optical waveguide on a head, measuring a blood flow of a brain, and displaying an image of an activity state of the brain on a monitor (Patent Document 1).

As another brain activity measuring apparatus, there has been an apparatus including an optical source to irradiate a living body with light, a light measuring unit including an optical transceiver which detects light with plural wavelengths emitted from the living body, a change measuring unit to measure a change over time of a specific component included in the blood according to a change in an amount of the transmitted light with the plural wavelengths, and a blood flow calculating unit to calculate a blood flow according to the change over time of the specific component and a proportion of the specific component in the blood (for example, see Patent Document 2). The apparatuses disclosed in Patent Documents 1 and 2 are also called optical topography apparatuses, whereby plural light emitting parts and light receiving parts are mounted on a head and an amount of transmitted light which has propagated inside a brain is detected by using near-infrared spectroscopy, so as to map an activity state of a brain function.

As blood flow measuring apparatuses to measure a blood flow of parts other than a brain, there has been an apparatus to measure a presence or absence of a blood clot. In this apparatus, the blood layer is irradiated with light and an amount of light which has transmitted through the blood layer is measured to detect the blood clot (for example, see Patent Document 3).

By the methods to measure a blood flow by using a light emitting part and a light receiving part which form an optical waveguide, such as those employed by the apparatuses disclosed in Patent Documents 1 to 3, a change in amount of light transmitted through blood has been measured. However, an amount or density (hematocrit) of red blood cells, which varies in accordance with a brain activity, has not been measured. It is known that hemoglobin (Hb) included in red blood cells has a property to absorb and scatteringly reflect light, and its optical characteristics are influenced by a Hb density, oxygen saturation, and an optical path length in the blood. Therefore, by the method of measuring a blood flow by using the light measuring unit as described above, a measurement result is changed depending on two conditions: namely, hemoglobin included in red blood cells and oxygen saturation (an oxygen amount carried by the red blood cells).

Therefore, when oxygen saturation of blood is constant, a blood flow can be accurately measured based on an amount of transmitted light that depends on an amount or density (hematocrit) of red blood cells in the blood. However, when oxygen consumption is increased or decreased by activities of a brain and muscles, the oxygen saturation is changed by an oxygen partial pressure ($PaO_2$), which changes an optical absorption factor. As a result, there is a possibility in that a change of the amount of transmitted light caused by the change of oxygen saturation is also measured as a change of the blood flow.

[Patent Document 1] Japanese Patent Application Publication No. 2003-149137

[Patent Document 2] Japanese Patent Application Publication No. 2003-144401

[Patent Document 3] Japanese Patent Application Publication No. 2002-345787

In the case of measuring a blood flow in a blood vessel for supplying blood to a brain or muscles by using the measuring apparatuses disclosed in Patent Documents 1 through 3, it has been difficult to accurately measure an activity state of the brain and muscles since the oxygen saturation changes depending on the oxygen partial pressure in the blood, which changes when the brain or muscles are highly active.

When the activity of the brain becomes greater, oxygen consumption of the brain increases. Therefore, multiple capillaries supply blood to the brain. Thus, a blood flow of a predetermined region, where plural capillaries are present, is measured depending on the size of a sensor (diameter of a probe which forms an optical waveguide). However, in the case where blood flows with different oxygen saturations in the plural capillaries, the conventional blood flow measuring apparatus and brain activity measuring apparatus have also detected a change in an amount of transmitted light that is caused by the change of the oxygen saturation. Therefore, it has been difficult to accurately measure an activity state of the brain.

In the case of measuring a blood flow in a blood vessel of other than a brain, it has been difficult to accurately measure the blood flow when the oxygen saturation of blood is not constant. It is because the amount of transmitted light changes depending on factors of both the density (hematocrit) or amount of red blood cells and the oxygen saturation.

In view of the above-described circumstances, it is an object of at least one embodiment of the present invention to provide a blood flow measuring apparatus that solves the above problems and a brain activity measuring apparatus using the blood measuring apparatus.

To solve the above-described problems, the present invention provides the following measures.

SUMMARY OF THE INVENTION

According to one aspect of the present invention, a blood flow measuring apparatus includes a sensor unit including a light emitting part configured to emit light onto a measurement area and a light receiving part configured to receive the light transmitted through the measurement area; at least one more light receiving part configured to receive the light transmitted through the measurement area; and a control part configured to measure a blood flow state of the measurement area according to signals outputted by the light receiving parts. The light emitted by the light emitting part is received by the light receiving parts arranged at different distances from the light emitting part and the light receiving parts output the signals responsive to the received light. The control part measures the blood flow state of the measurement area by performing an arithmetic process to cancel a component of oxygen saturation in the blood, said component being included in the signals outputted by the light receiving parts.

DETAILED DESCRIPTION OF THE PREFERRED EMBODIMENTS

Hereinafter, preferred embodiments of the present invention are described with reference to the drawings.

Embodiment 1

Figure 1:
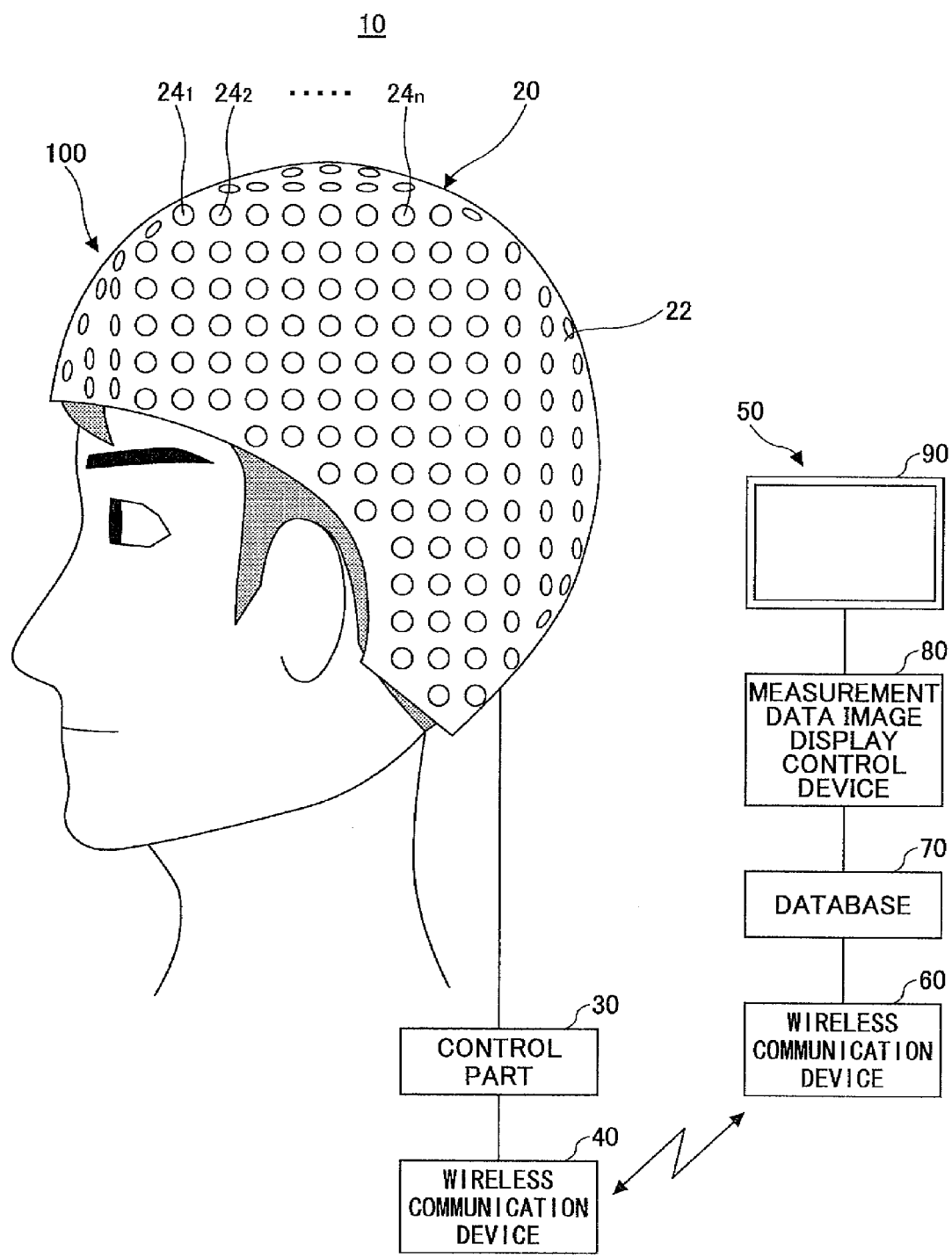
FIG. 1 illustrates a system configuration diagram showing an embodiment of a brain activity measuring apparatus using a blood flow measuring apparatus of the present invention.

FIG. 1 is a system configuration diagram showing an embodiment of a brain activity measuring apparatus using a blood flow measuring apparatus according to the present invention. As shown in FIG. 1, a brain activity measuring system 10 includes a brain activity measuring apparatus 100 and a data managing device 50 to manage measurement data collected by the brain activity measuring apparatus 100. Although FIG. 1 shows only one side of the brain activity measuring apparatus 100, an opposite side that corresponds to the back side of the drawing has a similar configuration.

The brain activity measuring apparatus 100 includes a blood flow measuring apparatus 20 mounted on a head, a control part 30 to measure the activity state (distribution of red blood cells) of a brain according to detection signals of an amount of transmitted light that is measured by the blood flow measuring apparatus 20, and a wireless communication device 40 to wirelessly send measurement results (blood flow data) outputted from the control part 30 to an external device.

The control part 30 stores a control program that performs such arithmetic processing (see arithmetic expressions described below) as to cancel a component of oxygen saturation, which is included in signals obtained from two or more light receiving parts.

The blood flow measuring apparatus 20 includes plural optical sensor units 24 ($24_1$ through $24_n$) which form an optical waveguide by irradiating a hat-shaped base 22 with light. In this embodiment, the sensor unit 24 has a diameter of about 10 to 50 mm. Therefore, about 150 to 300 sensor units 24 are attached in a predetermined arrangement pattern (at a predetermined interval) on the semispherical base 22. The plural sensor units 24 are independently managed in advance by address data corresponding to measurement positions of a subject to be measured. Measurement data obtained by the sensor units 24 are sent with respective address data and stored.

The plural sensor units 24 ($24_1$ to $24_n$) are preferably arranged in a matrix at a constant interval. However, the shape of a head to be measured is not constant but varies in size and curved surface shape. Therefore, the sensor units 24 may be arranged at an irregular interval as well.

The brain activity measuring apparatus 10 includes the wireless communication device 40 as an output unit. Therefore, in this embodiment, the brain activity measuring apparatus 10 is used in combination with a data managing device 50 which manages blood flow measurement data sent from the wireless communication device 40. However, the blood flow measurement data may be sent to another external device as well (for example, an electronic device such as a personal computer or a device to be controlled such as an actuator).

The data managing device 50 includes a wireless communication device 60 which receives the blood flow measurement data sent from the wireless communication device 40, a database 70 which stores the blood flow measurement data obtained from the wireless communication device 60, a measurement data image display control device 80 which forms image data according to the blood flow measurement data supplied through the database 70, and a monitor 90 to display the image data of the measurement results, which are generated by the measurement data image display control device 80.

The data managing device 50, which can wirelessly communicate with the brain activity measuring apparatus 100, can be set apart from the brain activity measuring apparatus 100. For example, the data managing device 50 can be set in a place where a subject cannot see the data managing device 50.

Figure 2A:
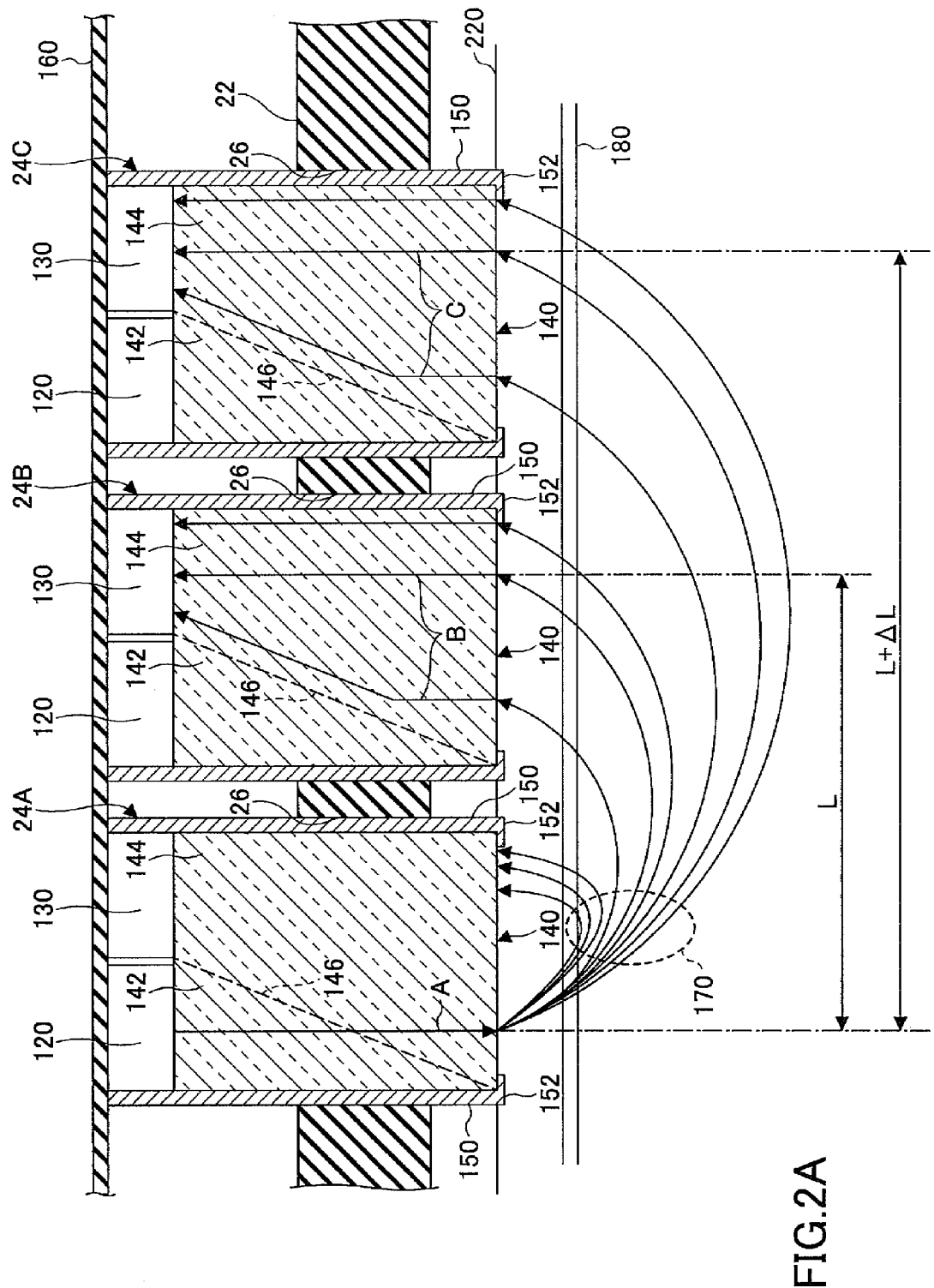
FIG. 2A illustrates an enlarged schematic diagram showing a longitudinal cross section of attached sensor units 24.

FIG. 2A is an enlarged diagram of an attachment structure of the sensor units 24. FIG. 2A shows a state where sensor units 24A, 24B, and 24C are mounted, among the plural sensor units 24. As shown in FIG. 2, the sensor units 24A, 24B, and 24C are inserted in attachment holes 26 of the semispherical base 22 which is flexible, and fixed by an adhesive and the like. Therefore, when the sensor units 24A, 24B, and 24C are fixed in the attachment holes 26 of the semispherical base 22, they are held so that their leading end parts contact a scalp surface 220 of the subject. The sensor units 24A, 24B, and 24C have the same configurations, in which the same components are denoted by the same reference numerals.

The sensor unit 24 includes a light emitting part 120 formed of a laser diode for irradiating the scalp surface 220 with a laser light (emission light) A, a light receiving part 130 formed of a light receiving element to output an electrical signal responsive to an amount of received transmitted light, and an optical path separating member 140 formed of a hologram which is constituted to have different refraction indexes with respect to the laser light A emitted by the light emitting part 120 to an area to be measured (measurement area), and to lights B and C incident through the measurement area, which proceeds to the light receiving part 130.

A brain wave measuring electrode 150 for measuring brain waves is fit on a peripheral surface of the optical path separating member 140. The brain wave measuring electrode 150 is formed in a cylindrical shape over a leading end surface and a side surface of the optical path separating member 140. A top end of the brain wave measuring electrode 150 is electrically connected to a wiring pattern of a flexible wiring board 160.

The top surfaces of the light emitting part 120 and the light receiving part 130 are mounted on a bottom surface side of the flexible wiring board 160. On the flexible wiring board 160, the wiring pattern connected to the control part 30 is formed. Connecting terminals of the light emitting part 120 and the light receiving part 130 are electrically connected to the wiring pattern at positions corresponding to the sensor units 24 by soldering and the like. The flexible wiring board 160 can be bent in accordance with the shape of a head when leading ends of the sensor units 24 contact the measurement area. In this manner, the flexible wiring board 160 is configured so as not to cause a broken wire when the base 22 is mounted or detached.

The brain wave measuring electrode 150 has a contact terminal 152 that is bent inward at a leading end. The contact terminal 152 protrudes from an end surface of the optical path separating member 140. Therefore, when the end surface of the optical path separating member 140 contacts the measurement area, the contact terminal 152 also contacts the measurement area, and can measure the brain waves. Further, the brain wave measuring electrode 150 can be also formed over a peripheral surface and a leading end edge part of the optical path separating member 140 by a method of applying a conductive film by a thin film forming method such as evaporation and plating. Moreover, the brain wave measuring electrode 150 may be formed of, for example, a transparent conductive film formed of indium tin oxide which is called ITO, over the peripheral surface and leading end edge part of the optical path separating member 140. When the brain wave measuring electrode 150 is formed of this transparent conductive film, the brain wave measuring electrode 150 becomes capable of transmitting light. Therefore, the entirety of the peripheral surface and the leading end surface of the optical path separating member 140 can be covered with the brain wave measuring electrode 150.

Normally, brain waves cannot be measured at the same time as measuring the blood flow by taking a laminagram of the brain and the like. However, by providing the brain wave measuring electrode 150 for the sensor unit 24, it becomes possible to measure the blood flow and brain waves simultaneously. Thus, it becomes possible to analyze a correlation between the blood flow and brain waves of the brain in details.

When measuring the blood flow, the control part 30 selects an arbitrary sensor unit 24 among the plural arranged sensor units 24 so as to emit the laser light A from the light emitting part 120 of the selected sensor unit 24. At this time, the laser light A emitted from the light emitting part 120 is outputted with a wavelength $\lambda$ ($\lambda \approx 805$ nm), which is not influenced by the oxygen saturation.

The sensor units 24 are held with their leading ends (the end surfaces of the optical path separating members 140) contacting the measurement area of a head. The laser light A is incident from the light emitting part 120 and proceeds through the optical path separating member 140 toward a scalp of the head into the brain in an orthogonal direction. Inside the brain, the laser light A proceeds toward the center of the brain while the laser light A propagates toward a periphery along a surface of the brain from the incident position as a base point. Optical propagation paths 170 of the laser light A inside the brain are formed in circular arcs when seen from a side of the head, pass through a blood vessel 180 of the head, and return to the scalp surface 220.

In this manner, the light which passes through the optical propagation paths 170 reaches the sensor units 24B and 24C on a light receiving side, while changing into transmitted light with an amount responsive to an amount or density of red blood cells included in blood which flows through the blood vessel 180. Further, the laser light A gradually decreases in the amount of transmitted light in a process of propagating inside the brain. Therefore, a light receiving level of the light receiving part 130 is decreased in proportion to a distance from the incident position of the laser light A. Thus, the amount of received transmitted light also changes depending on the distance from the incident position of the laser light A.

In FIG. 2A, when the sensor unit 24A positioned at a left end is used as a base point on a light emission side, the sensor unit 24A, the sensor unit 24B adjacent on the right of the sensor unit 24A, and the sensor unit 24C adjacent on the right of the sensor unit 24B correspond to base points on the light receiving side (measurement points).

The optical path separating member 140 is formed so as to make the laser light A proceed straight and guide the incident lights B and C to the light receiving parts 130 by, for example, changing the density distribution of a transparent acrylic resin. Further, the optical path separating member 140 includes an emission side transmitting area 142 which lets the laser light A emitted from the light emitting part 120 transmit from a base end side (top surface side in FIG. 2A) to a leading end side (bottom surface side in FIG. 2A), an incident side transmitting area 144 which lets the light propagated in the brain transmit from the leading end side (bottom surface side in FIG. 2A) to the base end side (top surface side in FIG. 2A), and a refraction area 146 formed between the emission side transmitting area 142 and the incident side transmitting area 144. This refraction area 146 has a property to transmit the laser light A and reflect light (incident lights B and C) which has transmitted through a blood flow. The refraction area 146 is formed by, for example, changing the density of the acrylic resin, providing a metal thin film, and dispersing metal microparticles in this area. Accordingly, lights incident from the leading ends of the optical path separating members 140 are all gathered at the corresponding light receiving parts 130.

Figure 2B:
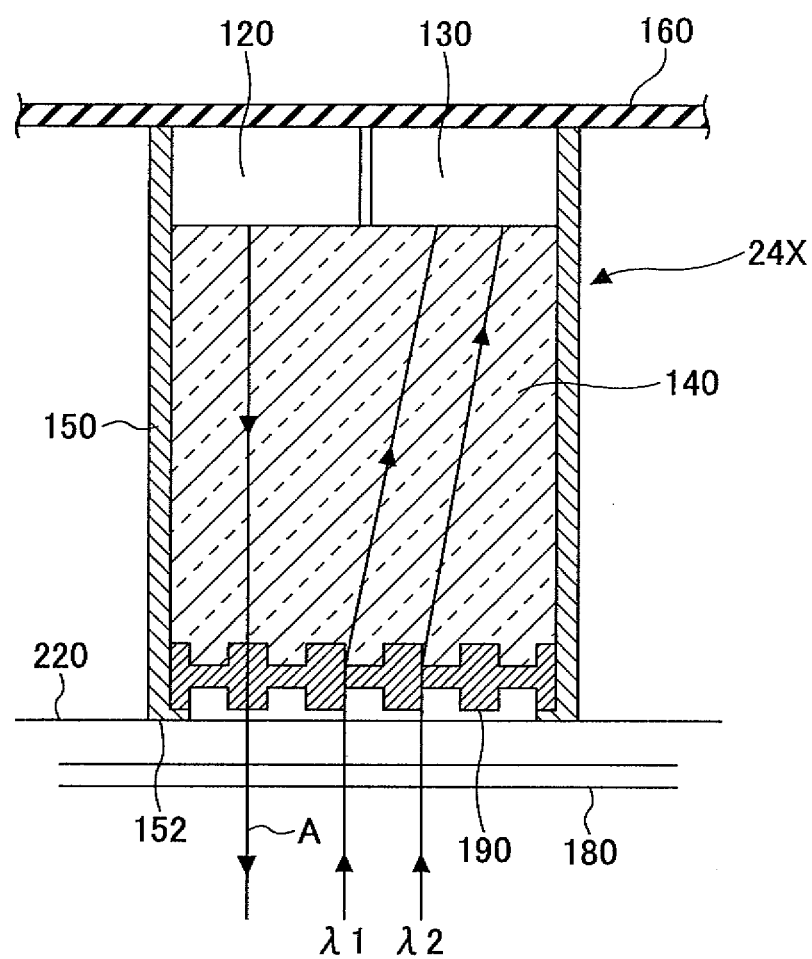
FIG. 2B illustrates a schematic diagram showing a longitudinal cross section of a variation example of the sensor unit 24.

FIG. 2B is a diagram showing a cross section of a variation example of the sensor unit 24. As shown in FIG. 2B, a sensor unit 24X of the variation example is provided with a diffraction grating 190 at a lower end of the optical path separating member 140. A bottom surface side peripheral edge part of the diffraction grating 190 is held by the contact terminal 152 which is formed by bending the leading end of the brain wave measuring electrode 150 inward. The diffraction grating 190 has a pattern with fine protrusions and recesses on front and back surfaces. The diffraction grating 190 is an optical element constituted so that incident light from the scalp surface 220 is diffracted toward the light receiving part 130 by a diffraction effect when passing through a border part of the pattern with protrusions and recesses.

Here, a principle of a blood flow measuring method is described.

Figure 3:
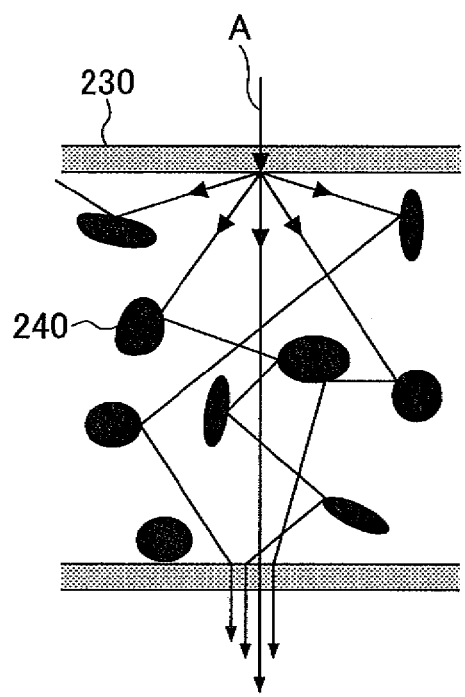
FIG. 3 illustrates a diagram for describing a principle of a blood flow measuring method.

FIG. 3 is a diagram for describing the principle of the blood flow measuring method. As shown in FIG. 3, when blood is irradiated with the laser light A externally, the laser light A incident into a blood layer 230 transmits through the blood as light having both components: namely, a normal light component scatteringly reflected by red blood cells 240 and a light component scatteringly reflected by an attached blood clot.

In transmitting through the blood layer 230, the laser light A receives an influence that constantly changes depending on the state of the blood. Therefore, by continuously measuring an amount of transmitted light (may be an amount of reflected light) to observe the change of the amount of light, changes of various properties of the blood can be observed.

When the activity of the brain increases, the brain consumes more oxygen. Therefore, the blood flow state, which is changed by the hematocrit of red blood cells which carry oxygen and oxygen saturation of the blood, causes a change of the amount of light.

Here, changes of the hematocrit (Hct: a volume ratio of red blood cells per unit volume, that is, a volume concentration of red blood cells per unit volume, also referred to as Ht) and the like are also related to a change of the density of hemoglobin and influence the change of the amount of light. A basic principle of this embodiment is to use the laser light A to measure a blood flow state according to a change of an optical path and an amount of transmitted light in the blood flow, and further to measure the activity of a brain according to the blood flow state of the brain.

A configuration of the present invention is described below. Optical characteristics of blood are determined by blood cell components (especially hemoglobin in erythroid cells). Moreover, red blood cells have a property in that hemoglobin is easily coupled to oxygen. Therefore, the red blood cells also have a role to carry oxygen to brain cells. Oxygen saturation in blood is a value that indicates a percentage of hemoglobin coupled to oxygen in the blood. The oxygen saturation which is correlated to an oxygen partial pressure ($PaO_2$) in arterial blood is an important index for a respiratory function (gas exchange).

It is known that the oxygen saturation is increased when the oxygen partial pressure becomes higher. When the oxygen saturation changes, the amount of light which transmits through blood changes as well. Therefore, a blood flow can be accurately measured by removing the influence of the oxygen saturation.

As factors having influences on the oxygen partial pressure ($PaO_2$), there is alveolar ventilation. Further, there are environmental factors such as atmospheric pressure and a fraction of inspiratory oxygen ($FiO_2$), and gas exchange in alveolar such as a ventilation/blood flow ratio, gas diffusion capacity, and a shunt rate.

The control part 30 includes an arithmetic unit which processes signals responsive to the amounts of transmitted light (light intensities), which are generated by the light receiving parts 130 of the sensor units 24A, 24B, and 24C. This arithmetic unit performs an arithmetic process to detect a blood flow state according to measurement values outputted by the light receiving parts 130 of the sensor units 24B and 24C as described below.

The laser light A is emitted by the light emitting part 120 as a pulsed light that is emitted intermittently at a predetermined time interval (for example, 10 Hz to 1 MHz) or a continuous light. In this case, when the pulsed light is employed as the laser light A, a pulse frequency at which the pulsed light flashes is determined by the speed of the blood flow. In that case, measurement is performed continuously or at a measurement sampling frequency which is twice or more of the pulse frequency of the laser light A. When the continuous light is employed as the laser light A, measurement is conducted at a measurement sampling frequency determined by the speed of the blood flow.

Hemoglobin (Hb) in blood chemically reacts with oxygen in lungs by respiration and become $HbO_2$; thereby the oxygen can be taken into the blood. Depending on respiration and the like, however, the degree of oxygen taken into the blood (oxygen saturation) is slightly different. That is, in connection with the present invention, such a phenomenon was found that when light is emitted into blood, optical absorptance of the blood changes depending on the oxygen saturation. This phenomenon is a disturbance element in measurement of a blood flow using the laser light A. Thus, the influence of the oxygen saturation is to be removed in the present invention.

Figure 4:
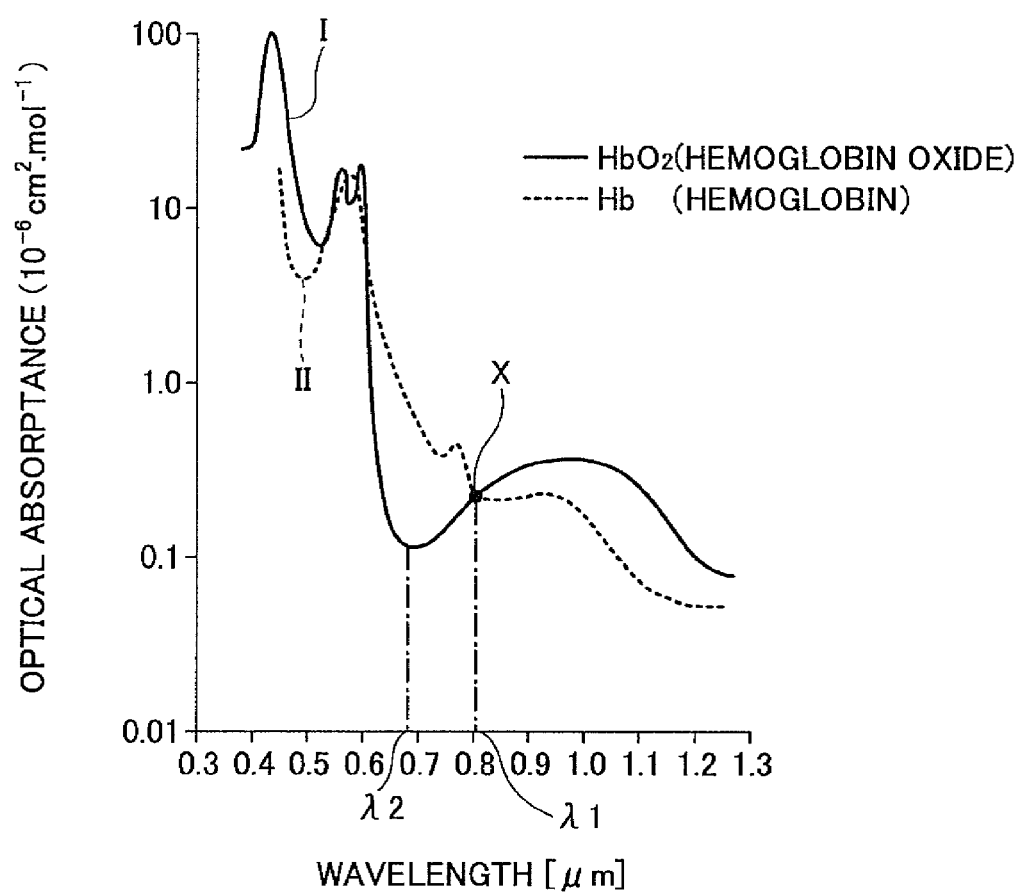
FIG. 4 illustrates a graph showing a relationship between the wavelength of laser light and optical absorptance in the case where oxygen saturation of blood is changed.

FIG. 4 is a graph showing a relationship between a wavelength of the laser light A and optical absorptance of the case where the oxygen saturation of blood is changed. Hemoglobin included in red blood cells is divided into hemoglobin oxide coupled to oxygen ($HbO_2$: graph II) and hemoglobin that is not oxidized (Hb: graph I) in a living body. Hemoglobin in these two states exhibit quite different optical absorptances with respect to light. For example, blood including sufficient oxygen is bright-colored as fresh blood. On the other hand, venous blood is dark colored since oxygen is released. These optical absorptances vary in a wide optical wavelength range as shown by the graphs I and II in FIG. 4.

It is found that a blood flow can be measured by irradiating blood with light without having an influence on the optical absorptance by selecting a specific wavelength from the graphs I and II in FIG. 4 even when the oxygen saturation of hemoglobin in red blood cells largely changes by oxygen metabolism in a living body and the like.

Regardless of the oxygen saturation of hemoglobin in red blood cells, the optical absorptance is small in a certain wavelength range. In this manner, it is determined whether the light at a wavelength $\lambda$ easily transmits through a blood layer. Therefore, when light in a predetermined wavelength range (for example, $\lambda$=about 800 nm to about 1300 nm) is used, a blood flow can be measured by suppressing an influence of the oxygen saturation.

Therefore, the laser light A in a wavelength range of about 600 nm to about 1500 nm is used in the present invention. Accordingly, the optical absorptance of hemoglobin (Hb) can be practically kept low enough. Moreover, since this range includes an isosbestic point X, the isosbestic point can be determined through calculation by using measurement points of two wavelengths or more. That is, a specification which is not influenced by the oxygen saturation can be made. In other wavelength ranges, S/N (Signal to Noise ratio) is decreased since the optical absorptance increases when λ=less than 600 nm. When λ=more than 1500 nm, a light receiving sensitivity of the light receiving part 130 is not sufficient and there is an influence of a disturbance such as other components in blood. Thus, a measurement with high precision cannot be performed in this case.

Therefore, in this embodiment, a light emitting element formed of a wavelength variable semiconductor laser is used as the light emitting part 120. Wavelengths of the laser light A emitted by the light emitting part 120 are set at λ1=805 nm (first light) which has the isosbestic point X in graphs I and II and at λ2=680 nm (second light) at which the optical absorptance is the lowest in graph Here, a description is made of a method for detecting red blood cell concentrations R, Rp, and Rpw. In this method, the red blood cell concentrations R, Rp, and Rpw are detected according to the amounts of transmitted light in the case of receiving the laser light A propagated through the optical propagation path 170 (see FIG. 2A).

An arithmetic expression (1) of the red blood cell concentration R by using a one-point-one-wavelength method employed in a conventional measuring method can be expressed as the following expression.

$$R=\log 10(Iin/Iout)=f(Iin,L,Ht) \quad (1)$$

By the method as expressed in expression (1), the red blood cell concentration corresponds to a function of an amount Iin of incident transmitted light of the laser light A emitted by the light emitting part 120, a distance (optical path length) L between the light emitting part 120 and the light receiving part 130r and the hematocrit (Ht). Iout denotes an amount of transmitted light of the laser light A received by the light receiving part 130. Therefore, it is difficult to accurately calculate the red blood cell concentration by the method of expression (1) since the red blood cell concentration changes depending on the above-described three factors.

An arithmetic expression (2) of the red blood cell concentration Rp by using a two-point-one-wavelength method according to this embodiment is expressed as the following expression.

$$Rp=\log 10\{Iout/(Iout-\Delta Iout)\}=\phi(\Delta L, Ht) \quad (2)$$

By the method as expressed in expression (2), propagated light of the laser light A is received at two points (the light receiving parts 130 of the sensor units 24B and 24C) set at different distances from the incident point of the laser light A as shown in FIG. 2. In the expression, Iout denotes an amount of light received by the light receiving part 130 which is closer to the light emitting part while (Iout−Δout) denotes an amount of light received by the light receiving part 130 which is further from the light emitting part 120, in which ΔIout denotes a difference (change) in the amount of received light between the two light receiving parts 130. Therefore, the red blood cell concentration Rp is obtained as a function of a distance ΔL between the two light receiving parts 130 and the hematocrit (Ht). Thus, since the distance ΔL between the two light receiving parts 130 is known in advance among the two factors, the red blood cell concentration is measured as a value having the hematocrit (Ht) as a coefficient, in the case of using expression (2) to calculate the red blood cell concentration. Accordingly, by this calculating method, the red blood cell concentration can be accurately measured as a measurement value responsive to the hematocrit (Ht).

Further, an arithmetic expression (3) of the red blood cell concentration Rpw by using a two-point-two-wavelength method according to a variation example of this embodiment can be expressed as the following expression.

$$Rpw=[\log 10\{Iout/(Iout-\Delta Iout)\}\lambda 1]/[\log 10\{Iout/(Iout-\Delta Iout)\}\lambda 2]=\xi(Ht) \quad (3)$$

By the method of expression (3), wavelengths of the laser light A emitted by the light emitting part 120 are set as λ1 and λ2 (λ1=805 nm while λ2=680 nm in this embodiment), which are different from each other. In the expression, Iout denotes an amount of light received by the light receiving part 130 which is closer to the light emitting part while (Iout−ΔIout) denotes an amount of light received by the light receiving part 130 which is further from the light emitting part 120, in which ΔIout denotes a difference (change) in the amount of received light between the two light receiving parts 130. Accordingly, the red blood cell concentration Rpw is calculated as a function of only the hematocrit (Ht). Therefore, according to this calculating method, the red blood cell concentration can be accurately measured as a measurement value responsive to the hematocrit (Ht).

Figure 5:
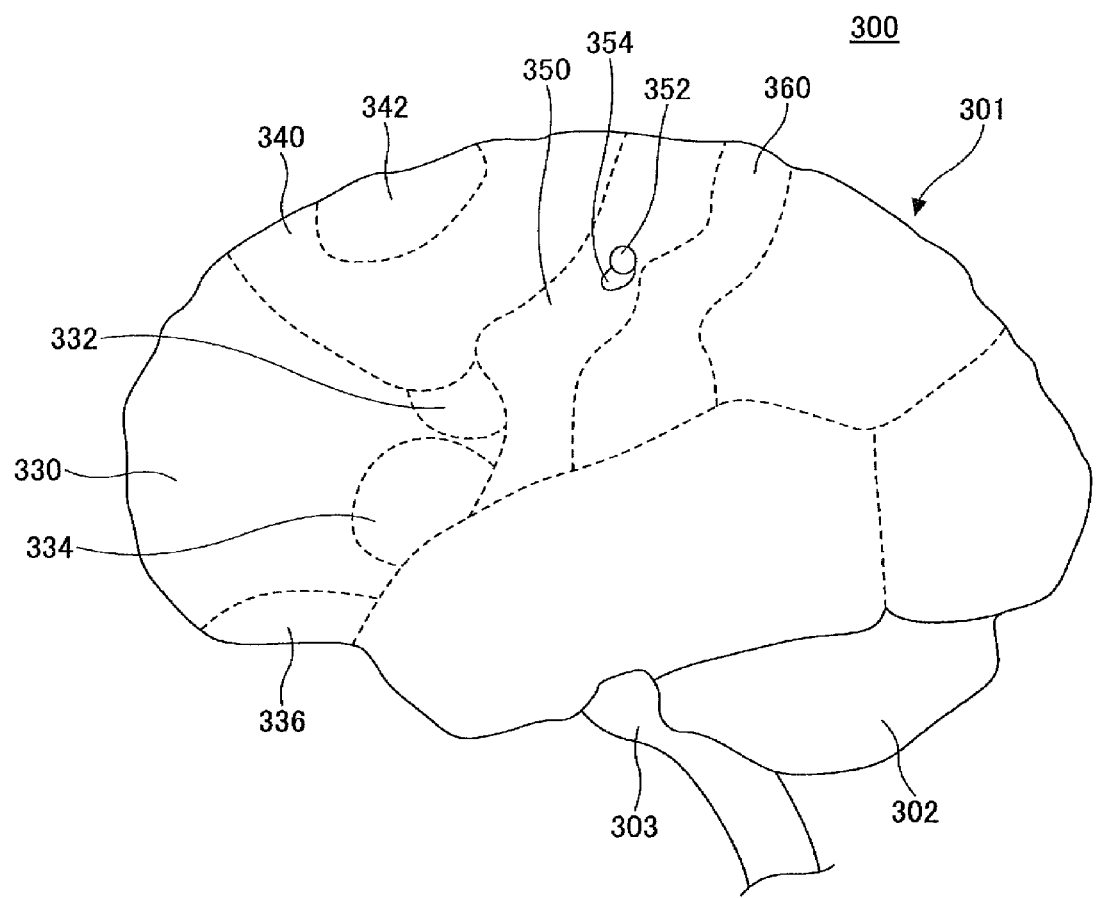
FIG. 5 illustrates a diagram of a brain seen from the left side.

Here, a brain to be used as a measurement area is described. FIG. 5 is a diagram of a brain seen from its left side. As shown in FIG. 5, a brain 300 of a human includes a cerebrum 301, a cerebellum 302, and a brainstem 303. The cerebrum 301 is a nerve center that controls motor functions of the human body. A cerebral cortex is divided into motor areas corresponding to the parts of the human body (joints of hands, elbows, shoulders, back, knees, ankles, and the like). For example, the brain 300 includes a prefrontal area 330, a premotor area 340, a motor area 350, a somatic sensory area 360, and the like. Moreover, the brain 300 has a frontal eye field 332, a Brocals area 334, and an olfactory area 336. The premotor area 340 has a motor association area 342.

Further, the motor area 350 manages movements of hands and feet. For example, the motor area 350 includes a shoulder motor area 352 and an elbow motor area 354. Therefore, by measuring blood flows of the shoulder motor area 352 and the elbow motor area 354 and mapping changes of the blood flows in each area, it can be detected how the shoulder and elbow are going to be moved.

Figure 6:
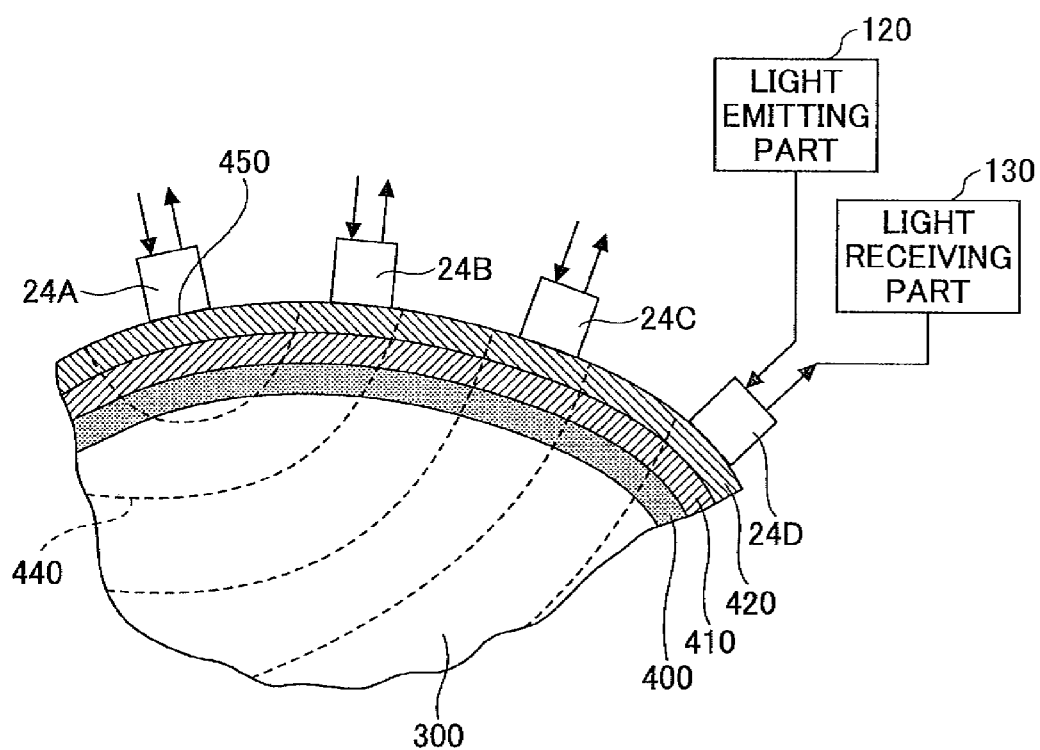
FIG. 6 illustrates a diagram for describing a principle of measuring brain activity according to blood flow of the brain.

FIG. 6 is a diagram showing a principle of measurement of brain activity according to a blood flow of the brain. As shown in FIG. 6, the brain 300 is covered with spinal fluid 400, a skull bone 410, and a scalp 420. The leading end surfaces of the optical path separating members 140 of the sensor units 24 are made to contact the scalp 420 so as to measure blood flows. The laser light A emitted by the light emitting part 120 of the sensor unit 24A proceeds into the brain 300 through the scalp 420, the skull bone 410, and the spinal fluid 400. The light emitted onto the head propagates in directions of an arcuate pattern 440 (directions of depths and radii) as shown by broken lines in FIG. 6.

When an optical propagation path of the laser light A becomes longer in accordance with a distance in the direction of the radius from a base point 450 on which the laser light is emitted, light transmittance becomes lower. Therefore, the sensor unit 24B, which is arranged adjacent to and at a predetermined distance from the sensor unit 24A on a light emission side, has a high light receiving level (amount of transmitted light). The sensor unit 24C, which is provided adjacent to and at a predetermined distance from the sensor unit 24B, has a light receiving level (amount of transmitted light) that is lower than that of the sensor unit 24B. Further, a light receiving part of the sensor unit 24A on the light emission side also receives light from the brain 300. Detection signals responsive to the intensities of light received by the plural sensor units 24 undergo a mapping process; thereby an optical intensity distribution responsive to the change of blood flow is obtained in a form of a striped graphic (contour lines).

When the detection signals (signals responsive to the amount of received transmitted light) outputted by the sensor units 24 are used as Iout of expression (2) or (3), the red blood cell concentration can be accurately measured as a measurement value responsive to the hematocrit (Ht) (that is, as a value which is not influenced by the oxygen saturation).

Figure 7:
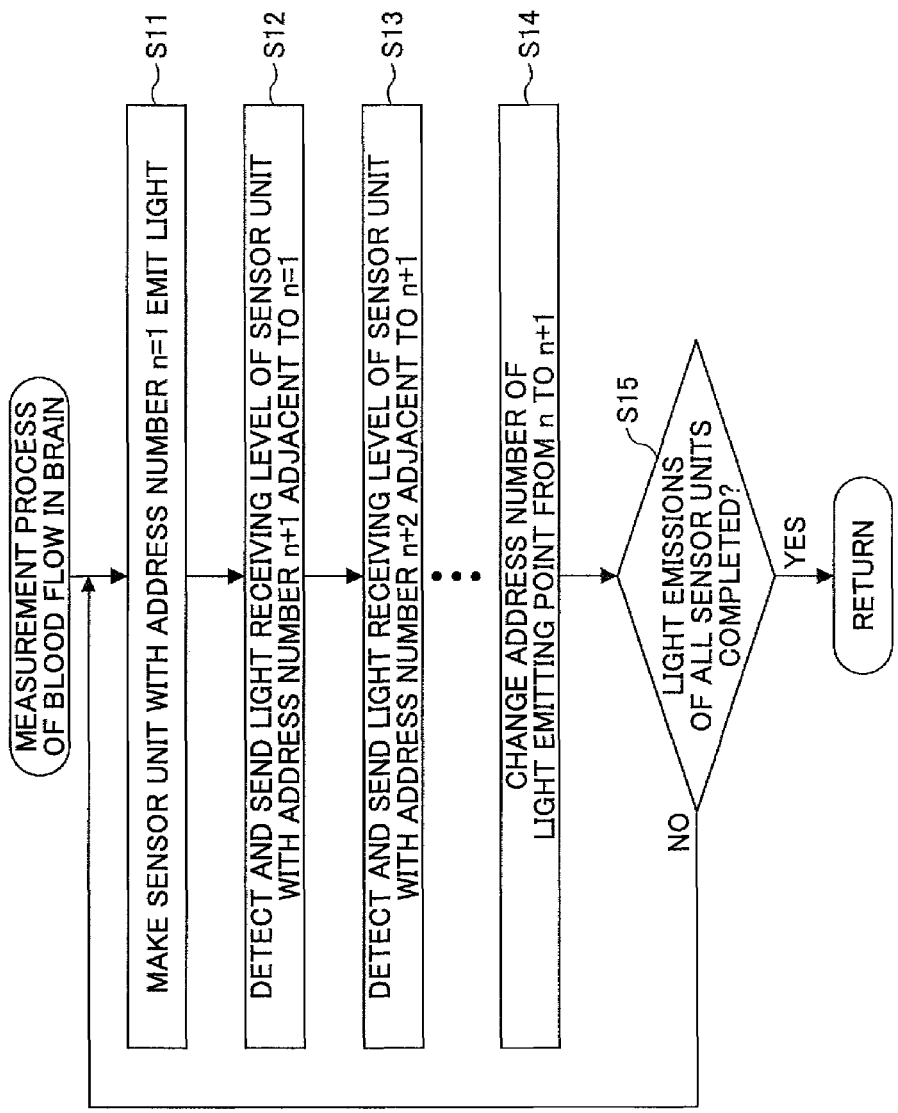
FIG. 7 illustrates a flowchart for describing a blood flow measuring process of a brain, which is performed by a control part 30 of a brain activity measuring apparatus 100.

Here, a measurement process of the blood flow (blood flow measurement process) of a brain, which is performed by the control part 30 of the brain activity measuring apparatus 100, is described with reference to FIG. 7. As shown in FIG. 7, the control part 30 performs the blood flow measurement process by dividing the cerebral cortex into measurement blocks corresponding to motor areas. For example, the control part 30 performs the blood flow measurement processes of measurement blocks of the prefrontal area 330, the premotor area 340, the motor area 350, and the somatic sensory area 360 in parallel. Here, for example, a description is made of the case of performing a blood flow measurement of the motor area 350 and performing a mapping process of the activity state of the motor area 350.

First, in step S11, the control part 30 selects an arbitrary sensor unit 24A (sensor unit with an address number n=1) among the plural sensor units 24 and makes the light emitting part 120 of the sensor unit 24A emit a laser light onto a measurement area (head area containing the motor area 350). Subsequently, in step S12, a detection signal (electric signal responsive to an amount of received transmitted light) outputted by the light receiving part 130 of the sensor unit 24B with an address number n=n+1, which is adjacent to the address number n=1, is sent from the wireless communication device 40 to the data managing device 50. The data managing device 50 stores data of the sensor unit 24B with the address number n=n+1, which is obtained from the wireless communication device 60, in the database 70.

In subsequent step S13, a detection signal (electric signal responsive to an amount of received transmitted light) outputted by the light receiving part 130 of the sensor unit 24C with an address number n=n+2, which is adjacent to the address number n+1, is sent from the wireless communication device 40 to the data managing device 50. The data managing device 50 stores data of the sensor unit 24C with the address number n=n+2, which is obtained from the wireless communication device 60, in the database 70.

In this manner, detection signals of all the sensor units 24 arranged around the sensor unit 24A which emits the laser light A as a base point, are sent to the data managing device 50.

In step S14, an address of the sensor unit to serve as a light emission point (base point) is changed to n+1. In step S15, it is determined whether all the sensor units 24 have emitted light. When all the sensor units 24 have not completed light emission in step S15, the laser light A is emitted by the light emitting part 120 of the sensor unit 24B having the address number n+1, and the processes of steps S11 to S15 are repeated.

In addition, in step S15, when all the sensor units 24 have completed light emission, the blood flow measurement process of this measurement block may be finished, or performed again from the beginning.

Figure 8:
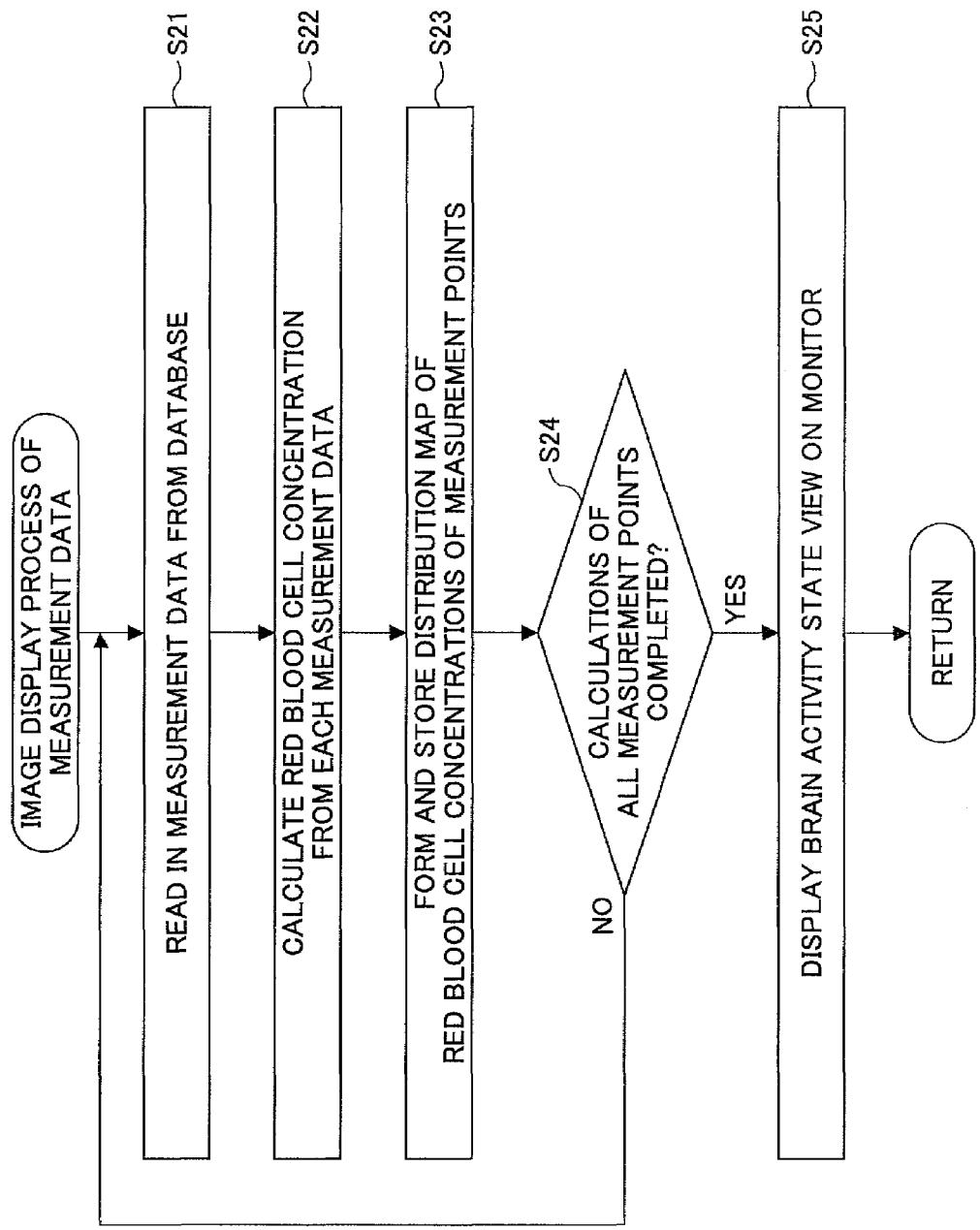
FIG. 8 illustrates a flowchart for describing a measurement data image display process performed by a measurement data image display control device 80 of a data managing device 50.

Here, with reference to FIG. 8, a description is made of an image display process of measurement data, which is performed by the measurement data image display control device 80 of the data managing device 50. The measurement data image display control device 80 reads in the measurement data (data of an amount of transmitted light responsive to a blood flow) stored in the database 70 in step S21 of FIG. 8. In step S22, the red blood cell concentration Rp or Rpw is calculated by using the measurement data and arithmetic expression (2) or (3).

In step S23, a distribution map (line map formed of contour lines) of the red blood cell concentrations at each measurement point is formed and image data of the distribution map are stored in the database 70. In step S24, it is determined whether the calculations of the red blood cell concentration Rp or Rpw of all the measurement points are completed. When the blood cell concentrations Rp or Rpw of all the measurement points have not been completed in step S24, the operation returns to step S21 to repeat the process from step S21.

When the red blood cell concentrations Rp or Rpw of all the measurement points are completed in step S24, the operation proceeds to step S25. In step S25, a brain activity state view showing a distribution of the red blood cell concentrations is displayed on a monitor 90.

In this manner, the red blood cell concentration Rp or Rpw is calculated from the measurement data according to the blood flow measured by the brain activity measuring apparatus 100, and the brain activity state based on a red blood cell concentration distribution of the measurement block is displayed on the monitor 90. Therefore, the brain activity state of the measurement area can be accurately determined.

Figure 9A:
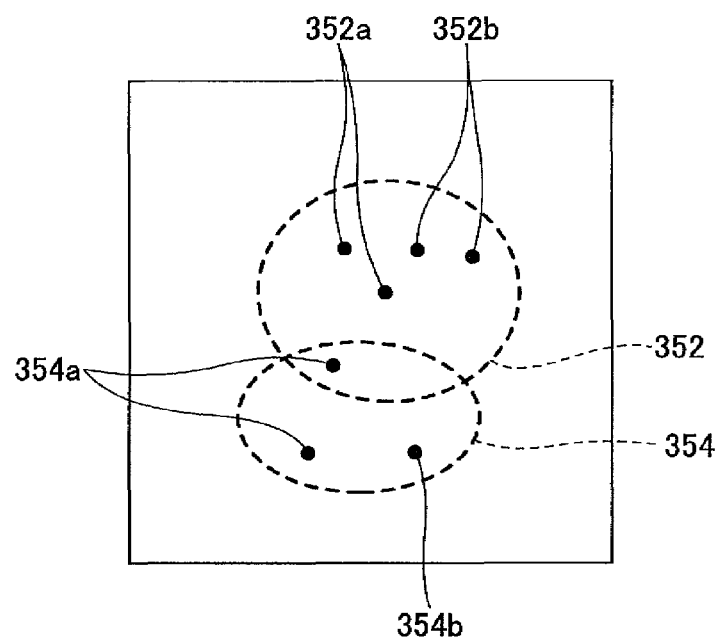
FIG. 9A illustrates a schematic diagram showing states of a shoulder motor area 352 and an elbow motor area 354 before measurement.
Figure 9B:
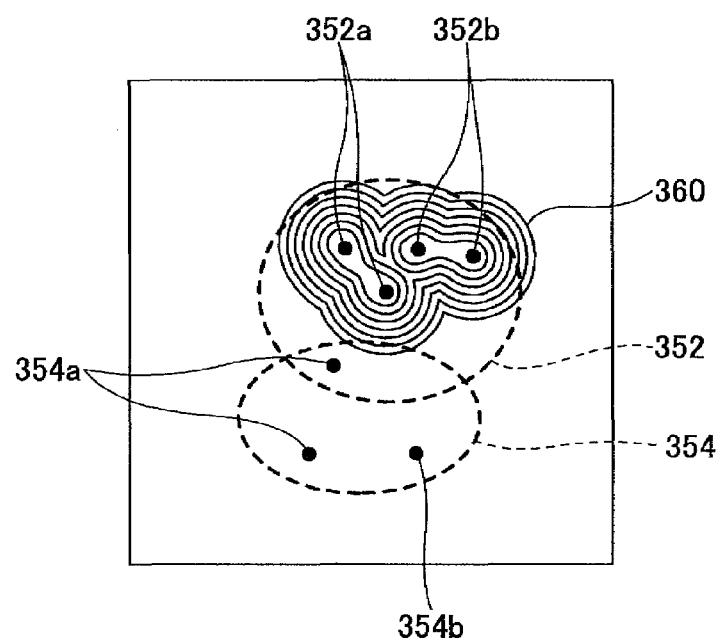
FIG. 9B illustrates a schematic diagram showing image data obtained from measurement data in the case of raising an arm.
Figure 9C:
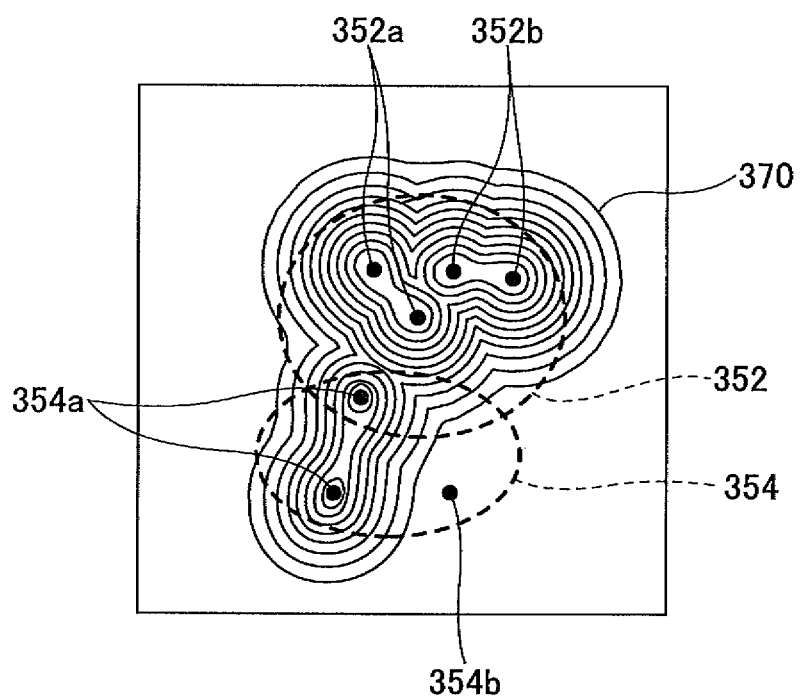
FIG. 9C illustrates a schematic diagram showing image data obtained from measurement data in the case of raising an arm with an elbow bent.

Here, a description is made of a display example of image data displayed by the measurement data image display control device 80. The image data are obtained as a measurement result of an amount of a blood flow (red blood cell concentration) of a brain by analyzing the measurement data sent from the brain activity measuring apparatus 100. FIG. 9A is a schematic diagram of the states of the shoulder motor area 352 and the elbow motor area 354 before measurement. FIG. 9B is a schematic diagram showing image data based on measurement data obtained when an arm is going to be raised. FIG. 9C is a schematic diagram showing image data based on measurement data obtained when an arm is going to be raised with an elbow bent.

As shown in FIG. 9A, the shoulder motor area 352 (area indicated by a broken line) of the brain 300 has adductor areas 352a and abductor areas 352b. The elbow motor area 354 (area indicated by a broken line) has flexion areas 354a and an extension area 354b of an elbow.

As shown in FIG. 9B, for example, when the brain 300 makes an order to raise an arm, image data of an activity area 360, that look like contour lines having the adductor areas 352a and abductor areas 352b of the shoulder motor area 352 as centers, are formed and displayed on the monitor 90. In this image data of the activity area 360, a dense part surrounded by many lines indicates high light intensity, which means that there is much blood flow. On the other hand, a coarse part surrounded by fewer lines indicates low light intensity, which means that there is little blood flow. As shown in the drawing of FIG. 9B, brain activities of the adductor areas 352a and the abductor areas 352*b* of the shoulder motor area 352 are activated. Thus, it can be known that the brain 300 is making an order to raise the arm.

As shown in FIG. 9C, for example, when the brain 300 makes an order to raise the arm with the elbow bent, image data of an activity area 370, that looks like contour lines having the adductor areas 352*a* and the abductor areas 352*b* of the shoulder motor area 352, and the flexion areas 354*a* of the elbow motor area 354 as centers, are formed and displayed on the monitor 90. In this activity area 370, a dense part surrounded by many lines indicates high light intensity, which means there is much blood flow. On the other hand, a coarse part surrounded by less lines indicates low light intensity, which means that there is little blood flow. As shown in the drawing of FIG. 9C, brain activities of the adductor areas 352*a* and the abductor areas 352*b* of the shoulder motor area 352 and the flexion area 354*a* of the elbow motor area 354 are activated. Thus, it can be known that the brain 300 is making an order to raise the arm with the elbow bent.

Figure 10A:
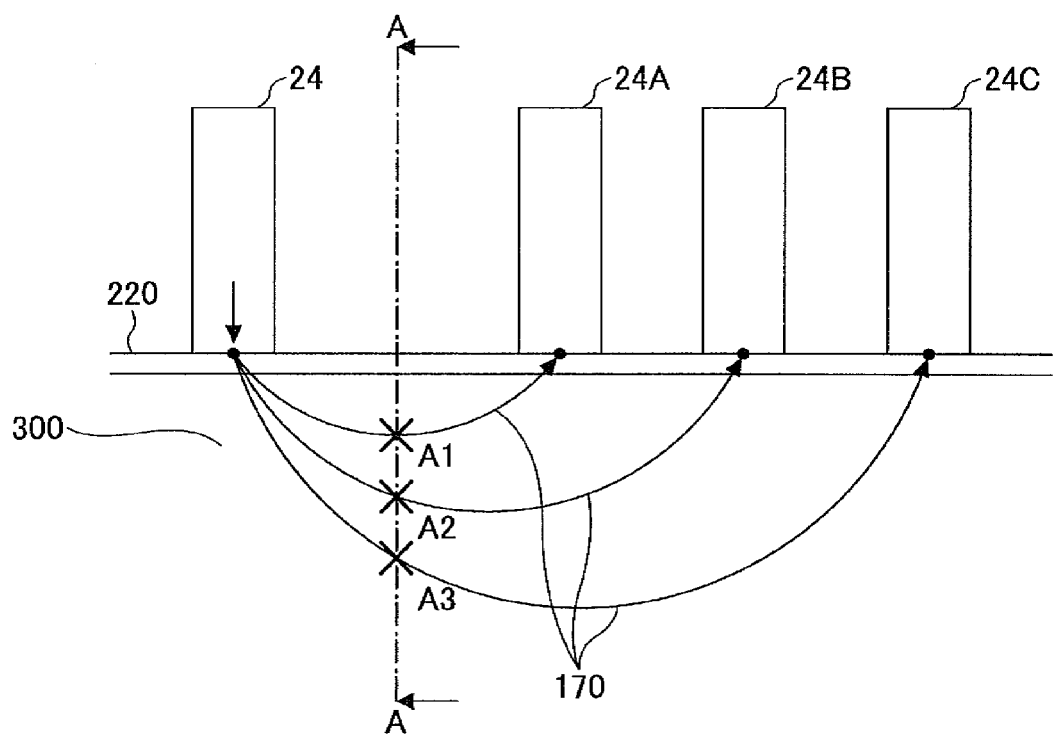
FIG. 10A illustrates a schematic diagram showing an optical propagation path of light emitted by a light emitting part 120.
Figure 10B:
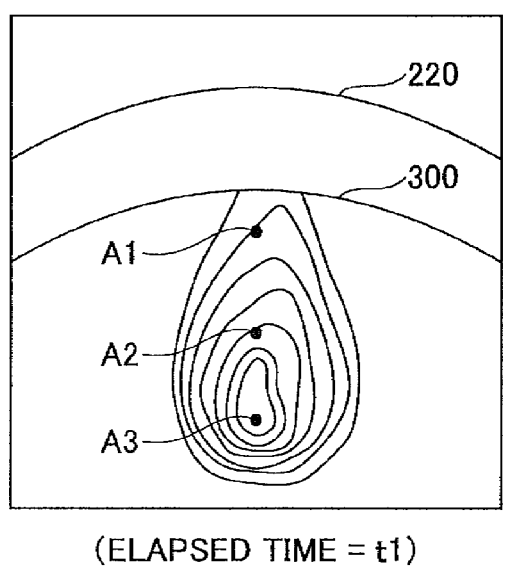
FIG. 10B illustrates a longitudinal cross-sectional diagram taken along a line A-A of FIG. 10A, showing a state right after (elapsed time t1) light irradiation by the light emitting part 120.
Figure 10C:
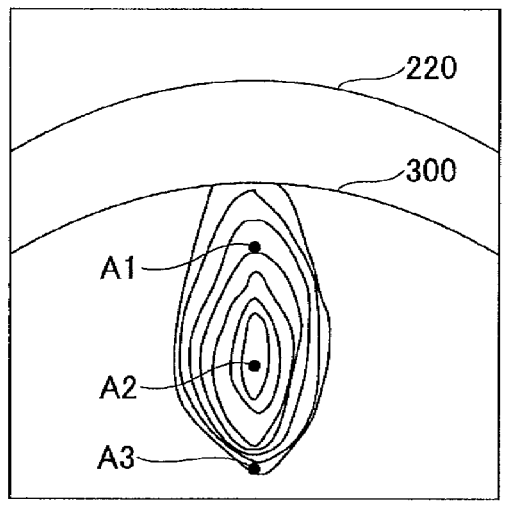
FIG. 10C illustrates a longitudinal cross-sectional diagram taken along a line A-A of FIG. 10A, showing a state after an elapsed time t2 from the light irradiation by the light emitting part 120.
Figure 10D:
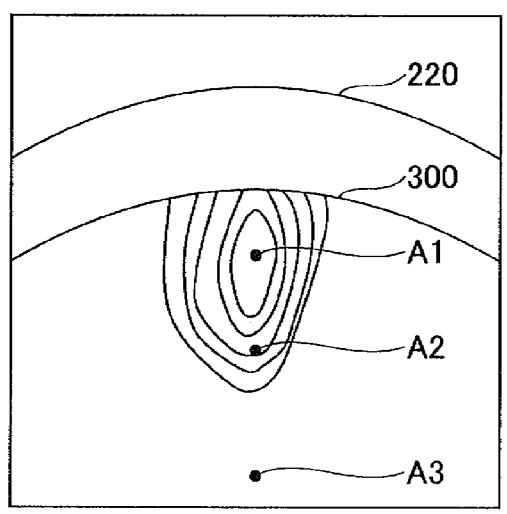
FIG. 10D illustrates a longitudinal cross-sectional diagram taken along a line A-A of FIG. 10A, showing a state after an elapsed time t3 from the light irradiation by the light emitting part 120.

Here, display examples of the measurement results of a blood flow in the direction of depth are described with reference to FIGS. 10A to 10D. FIG. 10A is a schematic diagram of an optical propagation path of light emitted by the light emitting part 120. FIG. 10B is a longitudinal cross-sectional diagram taken along a line A-A of FIG. 10A, which shows a state right after (elapsed time t1) the light irradiation by the light emitting part 120. FIG. 10C is a longitudinal cross-sectional diagram taken along the line A-A, which shows a state after an elapsed time t2 from the light irradiation by the light emitting part 120. FIG. 10D is a longitudinal cross-sectional diagram taken along the line A-A, which shows a state after an elapsed time t3 from the light irradiation by the light emitting part 120.

As shown in FIG. 10A, the laser light A emitted by the light emitting part 120 propagates, for example, by tracking a substantially arcuate trajectory as shown by the three optical propagation paths 170. Moreover, in FIGS. 10B through 10D, changes of light intensity at measurement points A1, A2, and A3, where the three optical propagation paths 170 and the line A-A intersect, are shown as images.

As shown in FIG. 10B, in the optical propagation paths 170 right after (elapsed time t1) the light irradiation by the light emitting part 120, it is seen that a blood flow amount (intensity of received light) at the measurement point A3 is detected to be the most.

As shown in FIG. 10C, in the optical propagation paths 170 after the elapsed time t2 from the light irradiation by the light emitting part 120, it is seen that a blood flow amount (intensity of received light) at the measurement point A2 is detected to be the most.

As shown in FIG. 10D, in the optical propagation paths 170 after the elapsed time t3 from the light irradiation by the light emitting part 120, it is seen that a blood flow amount (intensity of received light) at the measurement point A1 is detected to be the most.

In this manner, a distribution of amounts of blood flow in the direction of the depth can be measured according to the amounts of transmitted light at the measurement points A1, A2, and A3 arranged in the direction of the depth on the optical propagation paths 170. For example, in the cases of FIGS. 10B through 10D, it can be measured that the point at which there is the most amount of blood flow moves from inside the brain to a surface layer part of the brain over time.

Next, variation examples of the brain activity measuring apparatus 100 are described.

Figure 11A:
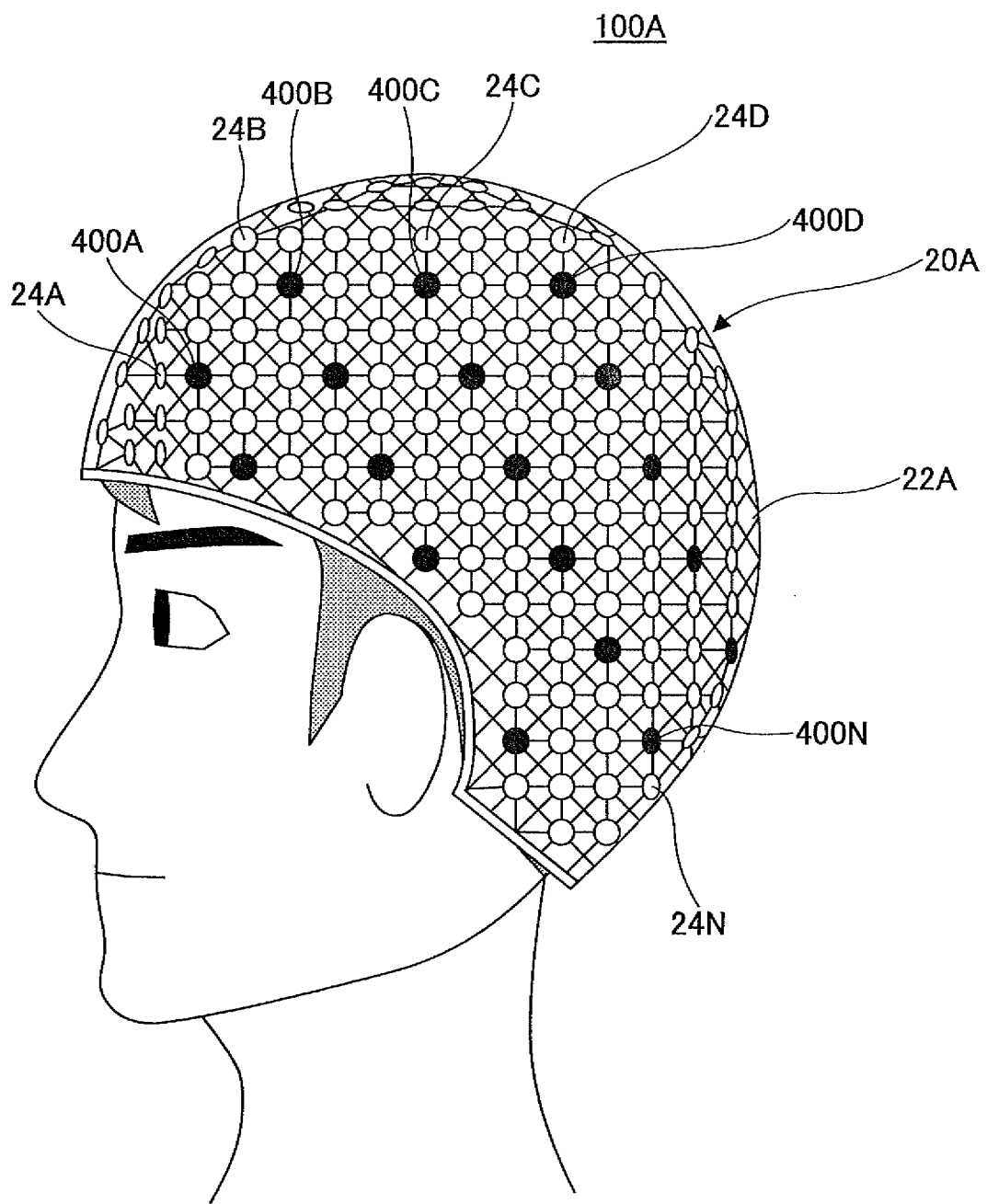
FIG. 11A illustrates a diagram showing a mounted brain activity measuring apparatus according to a variation example 1.

FIG. 11A is a diagram showing a mounted brain activity measuring apparatus 100A according to a variation example 1. As shown in FIG. 11A, a blood flow measuring apparatus 20A of the brain activity measuring apparatus 100A according to the variation example 1 has a spherically formed net-like base 22A to which plural sensor units 24 are attached. Although FIG. 11A shows only one side of the brain activity measuring apparatus 10A, an opposite side that corresponds to the back side of the drawing has a similar configuration.

The sensor units 24 are held passing through intersection parts of the net of the base 22A. Further, square-shaped coupling structures of the net-like base 22A are stretched and deformed into diamond shapes in accordance with the shape of a head surface on which the net-like base 22A is mounted. Therefore, the net-like base 22A can be deformed into a spherical shape corresponding to the shape of the head surface.

The net-like base 22A has (four to eight) net arm parts connected to the intersection parts, which are formed of a resin material having elasticity. Due to the elasticity of the material itself, end parts of the plural sensor units 24 can be tightly attached onto the head surface on which the net-like base 22A is mounted. Regardless of the shape of the head surface, the leading end parts of the plural sensor units 24 can be made to contact the head surface which is an object to be measured.

In the variation example 1, the sensor unit 24 has a diameter of about 10 mm to 50 mm. Therefore, about 150 to 300 sensor units 24 are attached on the net-like base 22A in a predetermined arrangement pattern (at a predetermined interval). The plural sensor units 24 are independently managed in advance by address data corresponding to measurement positions of the object to be measured in a manner similar to the embodiment 1. The measurement data obtained by the sensor units 24 are sent with respective address data to the data managing device 50 and stored.

The net-like base 22A is partitioned into plural blocks A through N, which have respective small wireless communication devices 400A through 400N (shown as black circles in FIG. 11A). The measurement data obtained by the plural sensor units 24 can be sent independently from the wireless communication devices 400A through 400N of the blocks A through N to the data managing device 50.

Figure 11B:
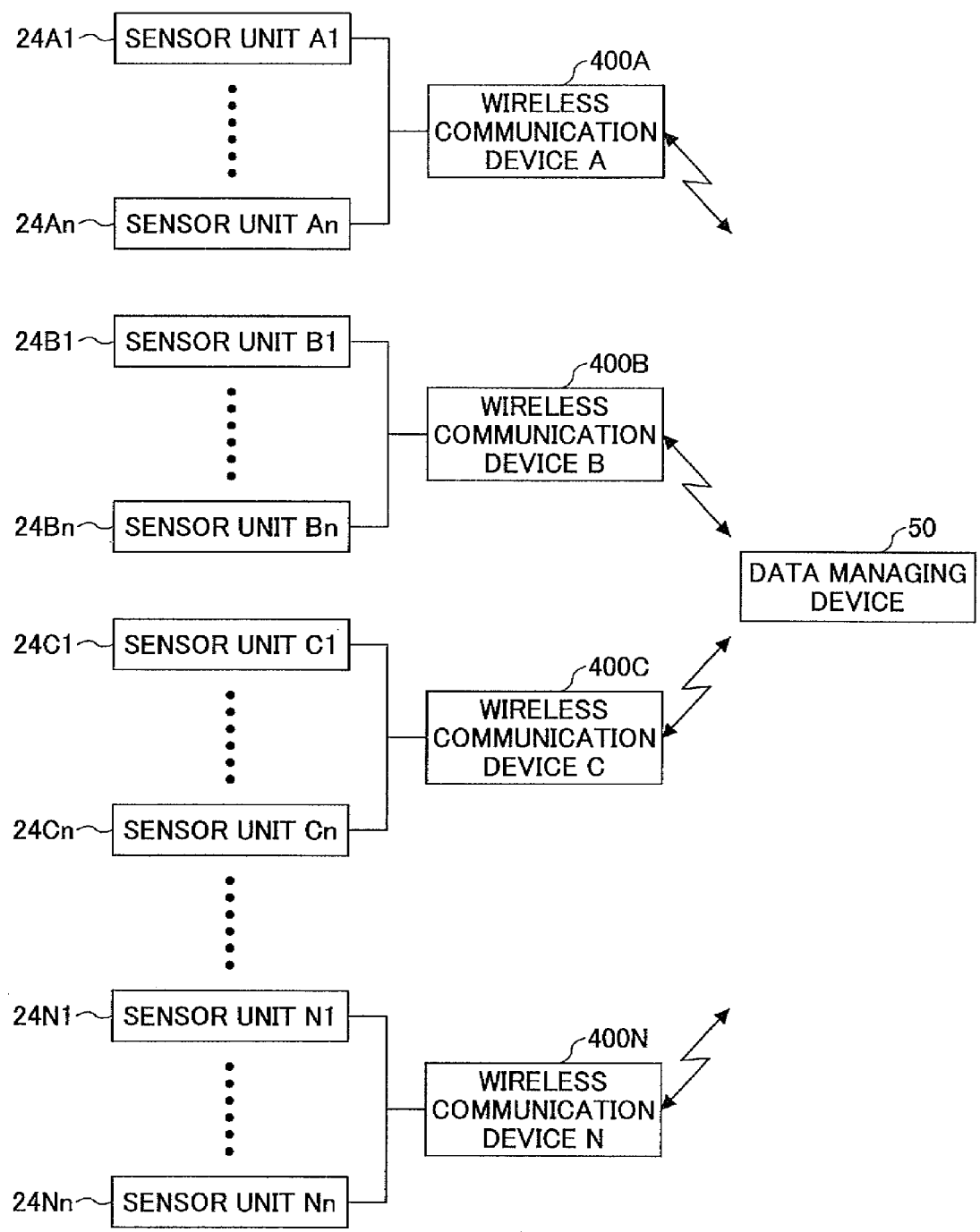
FIG. 11B illustrates a block diagram showing configurations of devices according to the variation example 1.

FIG. 11B is a block diagram showing configurations of devices of the variation example 1. As shown in FIG. 11B, the plural sensor units 24 are classified by, for example, blocks A through N that partition the brain 300 according to functions. For example, the sensor units 24 are grouped into sensor units 24A1 through 24An, 24B1 through 24Bn, . . . 24N1 through 24Nn. The wireless communication devices 400A through 400N provided in the blocks A through N send and receive wireless signals to/from the data managing device 50. Upon receiving an order of light emission from the data managing device 50, the wireless communication devices 400A through 400N output light emission signals to the sensor units 24 of the blocks A through N in parallel. Accordingly, the light emitting parts 120 of the blocks A through N sequentially irradiate the head surface (measurement area) of the blocks with the laser light. At the same time, measurement data responsive to the amount of transmitted light received by the light receiving parts 130 of the sensor units 24A1 through 24An, 24B1 through 24Bn, 24N1 through 24Nn provided in the blocks A through N are sent from the wireless communication devices 400A through 400N to the data managing device 50. Therefore, in the data managing device 50, the data of the blocks A through N, which have been measured by the sensor units 24A1 through 24An, 24B1 through 24Bn, . . . 24N1 through 24Nn, are processed in parallel.

In this variation example 1, the brain activity measuring apparatus 100A includes the plural wireless communication devices 400A through 400N. Therefore, the measurement data measured by the sensor units 24A1 through 24An, 24B1 through 24Bn, . . . 24N1 through 24Nn can be sent in a short time. Moreover, the data managing device 50 can analyze the measurement data of each of the blocks A through N and efficiently form image data of each of the blocks A through N in parallel.

Further, in the net-like base 22A, two arms of the plural arms connected to the intersection parts may be formed of a conductive material and connected to the light emitting part 120 and the light receiving part 130 of the sensor unit 24 so as to be used for ordering light emission and detecting the measurement data of the received light.

Figure 12:
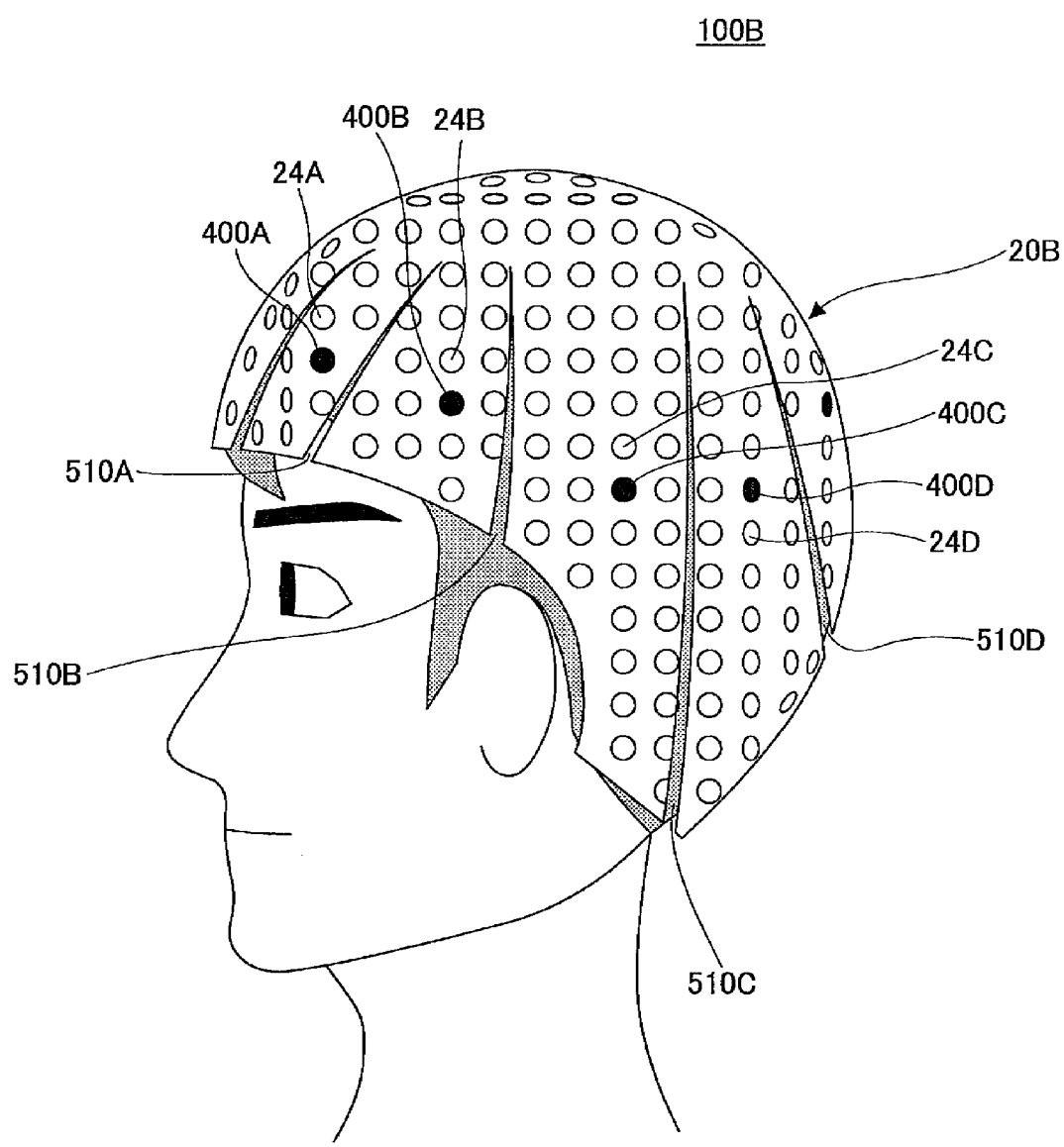
FIG. 12 illustrates a diagram showing a mounted brain activity measuring apparatus according to a variation example 2.

FIG. 12 is a diagram showing a mounted brain activity measuring apparatus 100B of a variation example 2. As shown in FIG. 12, a blood flow measuring apparatus 20B of the brain activity measuring apparatus 100B according to the variation example 2 has a flexible wiring board 500 formed of a resin material. The flexible wiring board 500 has plural slits 510A through 510N which are provided radially. Although FIG. 12 shows only one side of the brain activity measuring apparatus 100B, an opposite side that corresponds to the back side of the drawing has a similar configuration. Moreover, the flexible wiring board 500 holds the plural sensor units 24 arranged at a predetermined interval in a manner similar to embodiment 1.

Since the flexible wiring board 500 has flexibility, it can be easily deformed into a curved shape corresponding to the shape of the head surface due to the plural slits 510A though 510N. Moreover, by providing the plural slits 510A through 511N directed from an outline side to a central part of the flexible wiring board 500 which is formed in a flat shape and adjusting the cutting angles and cutting lengths of the slits, the flexible wiring board 500 can assume various curved shapes. Therefore, in this variation example 2, the flexible wiring board 500 can be easily mounted on the head surface by bending the flexible wiring board 500, and also can be easily detached from the head surface only by returning the flexible wiring board 500 into the flat shape after the measurement.

The plural sensor units 24 held by the flexible wiring board 500 are controlled in each area partitioned by the slits 510A through 510N, and grouped into, for example, the sensor units 24A1 through 24An, 24B1 through 24Bn, . . . 24N1 through 24Nn. Therefore, since the plural slits 510A through 510N can be provided at arbitrary positions, the area of each of the blocks A through N can be set in accordance with the corresponding measurement area.

In this variation example 2 as well, the small wireless communication devices 400A through 400N (shown as black circles in FIG. 12) are provided in the blocks A through N respectively. Therefore, the measurement data obtained by the plural sensor units 24 can be independently sent per blocks A through N from the corresponding wireless communication devices 400A through 400N to the data managing device 50.

Figure 13:
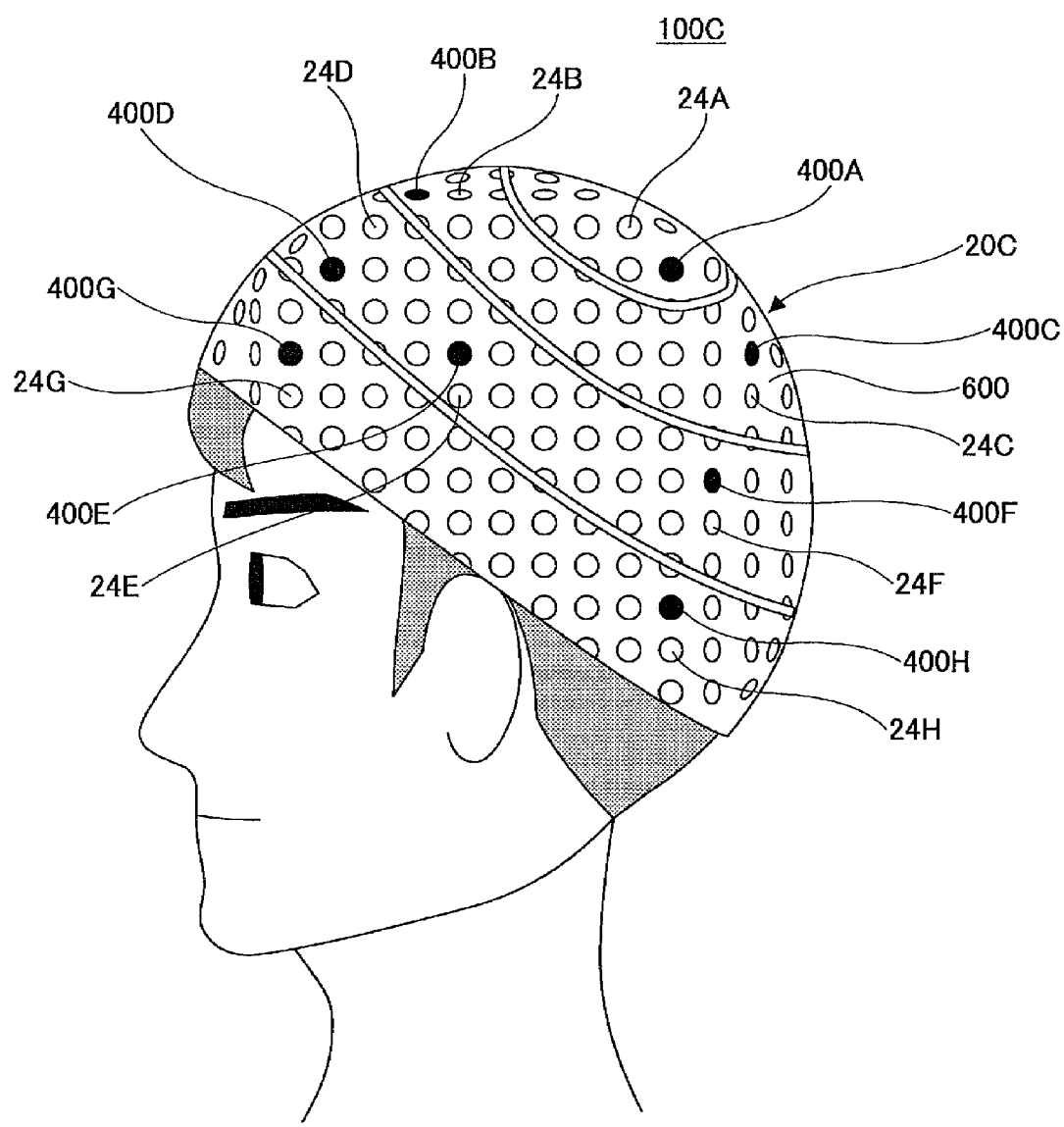
FIG. 13 illustrates a diagram showing a mounted brain activity measuring apparatus according to a variation example 3.

FIG. 13 is a diagram showing a mounted brain activity measuring apparatus 100C according to a variation example 3. As shown in FIG. 13, a blood flow measuring apparatus 20C of the brain activity measuring apparatus 100C of the variation example 3 is formed of a flexible wiring board 600 that is formed of a resin material in a belt shape and then wrapped around a head in a spiral manner. Although FIG. 13 shows only one side of the brain activity measuring apparatus 100C, an opposite side that corresponds to the back side of the drawing has a similar configuration. The flexible wiring board 600 holds the plural sensor units 24 and the wireless communication devices 400A through 400N (shown as black circles in FIG. 13) at a predetermined interval in a manner similar to the variation example 2.

Since the flexible wiring board 600 is formed in a belt shape with flexibility, it can be freely wrapped around the shape of the head surface, and can be easily mounted on the head so as to be tightly attached to the shape of the curved surface of the head. Although there are various shapes of heads of the subjects, the flexible wiring board 600 can be mounted on the heads of various shapes by appropriately adjusting a wrapping area of the flexible wiring board 600.

Figure 14:
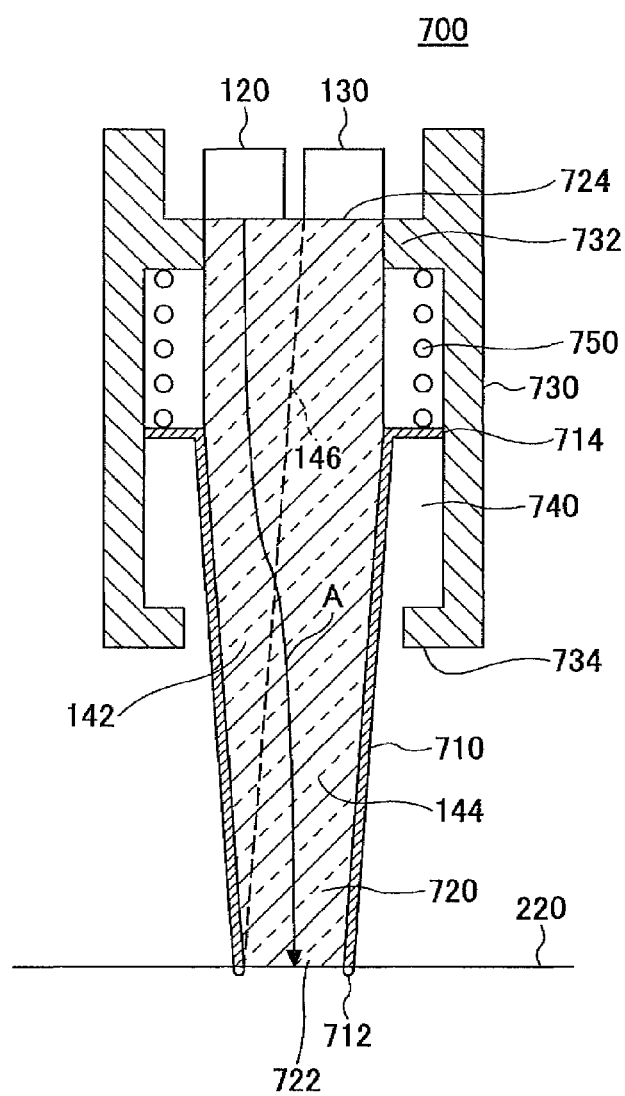
FIG. 14 illustrates a schematic diagram showing a longitudinal cross section of a variation example of a sensor unit.

FIG. 14 is a longitudinal schematic diagram showing a cross section of a sensor unit 700, which is a variation example of the sensor unit 24. In FIG. 14, the same components as those in the sensor unit 24 in FIG. 2 are denoted by the same reference numerals and description thereof is omitted here. In the sensor unit 700, as shown in FIG. 14, an optical path separating member 720 formed in a tapered shape is inserted and held in a brain wave measuring electrode 710 formed in a tapered cylindrical shape. In this embodiment, the brain wave measuring electrode 710 is fit on an outer periphery of the optical path separating member 720 in an integrated manner. Tapered angles of the brain wave measuring electrode 710 and the optical path separating member 720 are arbitrarily set depending on a whole length, areas of top and bottom end parts, and the like. The optical path separating member 720 is formed of a hologram in a manner similar to the embodiment 1. The optical path separating member 720 transmits the laser light emitted by the light emitting part 120 to a leading end part 722, and condenses the light which has propagated through the brain 300 and reentered from the leading end part 722 to the light receiving part 130.

A leading end part 712 of the brain wave measuring electrode 710 protrudes slightly downward from the leading end part 722 of the optical path separating member 720. Therefore, a brain wave of this measurement area can be measured by the leading end part 712 contacting the scalp surface 220.

A collar part 714 with a large diameter is provided on a base end side of the brain wave measuring electrode 710. This collar part 714 is inserted slidably in an axis direction (vertical directions) along an inner wall of an external cylindrical member 730 formed of a conductive material. The external cylindrical member 730 has a space 740 in which the brain wave measuring electrode 710 and the optical path separating member 720 are slid in the axis direction, a top wall part 732 formed so as to surround an upper part of the space 740, and a lower wall part 734 formed so as to surround a lower part of the space 740.

A biasing member (coil spring) 750 to bias the brain wave measuring electrode 710 downward is provided between the collar part 714 of the brain wave measuring electrode 710 and the upper wall part 732. When the leading ends of the brain wave measuring electrode 710 and the optical path separating member 720 contact the scalp surface 220, the biasing member 750 is compressed by the pressure force. By a repulsive force against the compression force, the front ends of the brain wave measuring electrode 710 and the optical path separating member 720 are pressed onto the scalp surface 220.

Therefore, by mounting the sensor unit 700 by pressing the external cylindrical member 730 downward, a biasing force of the biasing member 750 acts to tightly attach the leading ends of the brain wave measuring electrode 710 and the optical path separating member 720 onto the scalp surface 220. Therefore, even when there is hair on the measured area, the front ends of the brain wave measuring electrode 710 and the optical path separating member 720 can be made to surely contact the scalp surface 220.

On a top end surface 724 of the optical path separating member 720, the light emitting part 120 and the light receiving part 130 are mounted. The optical path separating member 720 of this variation example is formed in a tapered shape so that its top end has a large diameter. Therefore, an area of the top end surface 724 can be set in accordance with the sizes of the light emitting part 120 and the light receiving part 130. Moreover, the diameter of the leading end part 722 of the optical path separating member 720 can be reduced to make a contact area with the scalp surface 220 smaller, regardless of the sizes of the light emitting part 120 and the light receiving part 130. Accordingly, when the leading end surface 722 of the optical path separating member 720 contacts the scalp surface 220, a possibility of catching the hair is reduced and the precision of the measurement is enhanced.

In this embodiment, the laser light A emitted onto the scalp surface 220 and light received at the leading end part 722 of the optical path separating member 720 form a waveguide while being reflected on the tapered inner wall of the brain wave measuring electrode 710. Therefore, there is no influence on the amount of light transmitting through the optical separating member 720.

Embodiment 2

Figure 15:
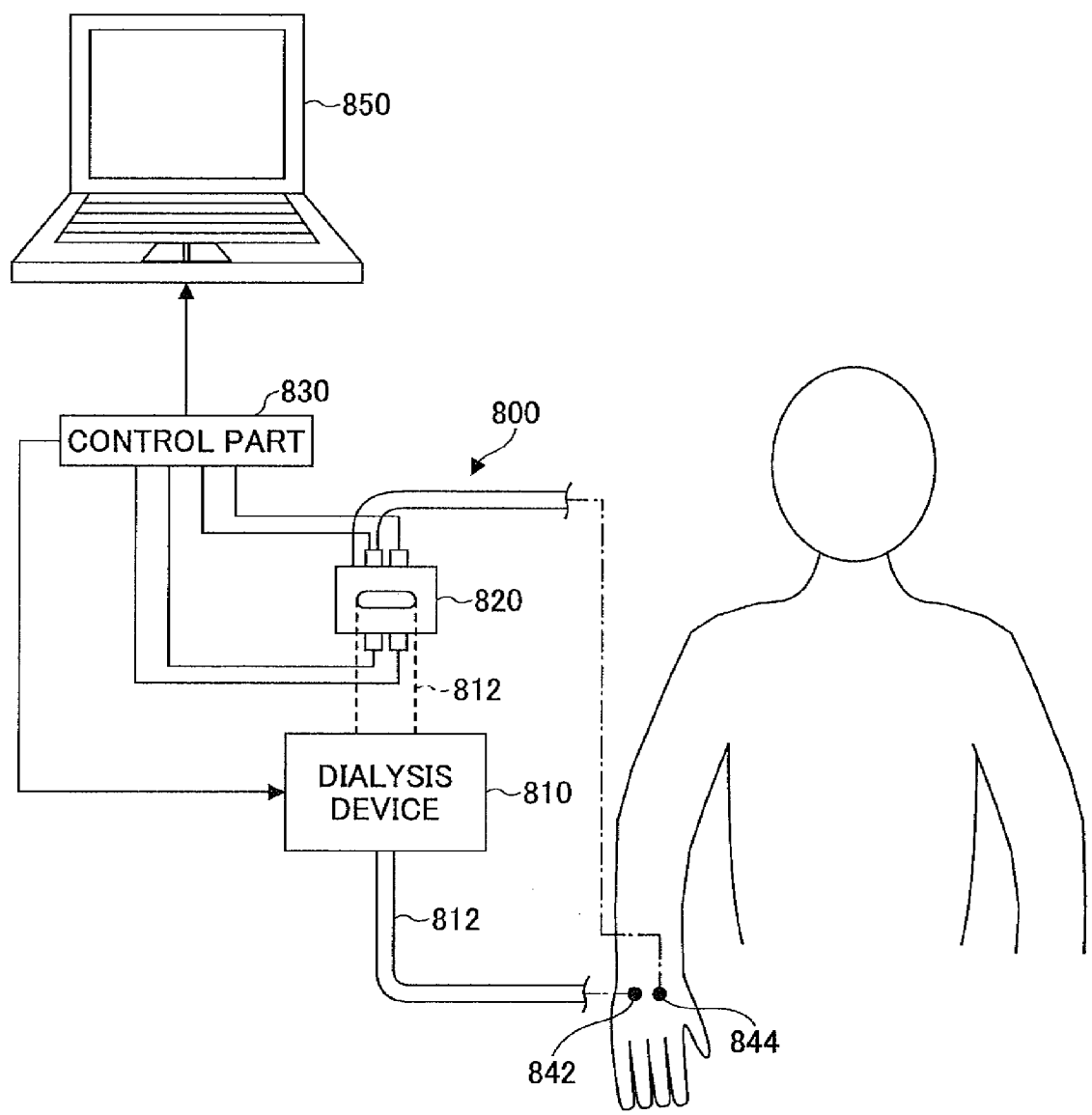
FIG. 15 illustrates a schematic diagram showing a configuration of a blood flow measuring apparatus of embodiment 2.

FIG. 15 is a systematic diagram showing a schematic configuration of a blood flow measuring apparatus 800 of embodiment 2. As shown in FIG. 15, the blood flow measuring apparatus 800 of embodiment 2 measures a blood flow amount in the case of dialysis treatment. The blood flow measuring apparatus 800 includes a sensor unit 820 mounted on a dialysis tube 812 connected to a dialysis device 810 and a control part 830 to control the dialysis device 810 according to measurement data outputted by the sensor unit 820.

The dialysis tube 812 is formed of a translucent resin tube with elasticity. The dialysis tube 812 is connected to blood vessels 842 and 844 of a patient 840 who takes dialysis treatment. Blood taken out of the blood vessels 842 and 844 is supplied through the dialysis tube 812 to the dialysis device 810. The dialysis device 810 includes an artificial kidney (dialyzer) to filter the blood and supply dialysate, and a pump device to send the blood.

The control part 830 calculates a blood flow amount and a red blood cell concentration according to measurement data measured by the sensor unit 820, controls the amount of dialysate to be supplied and a pump rotational speed of the dialysis device 810 according to the blood flow amount. Moreover, the control part 830 outputs measurement results of the sensor unit 820 and dialysis data to a personal computer 850. The personal computer 850 performs accumulation, analysis, and the like of the measurement results and dialysis data.

Figure 16:
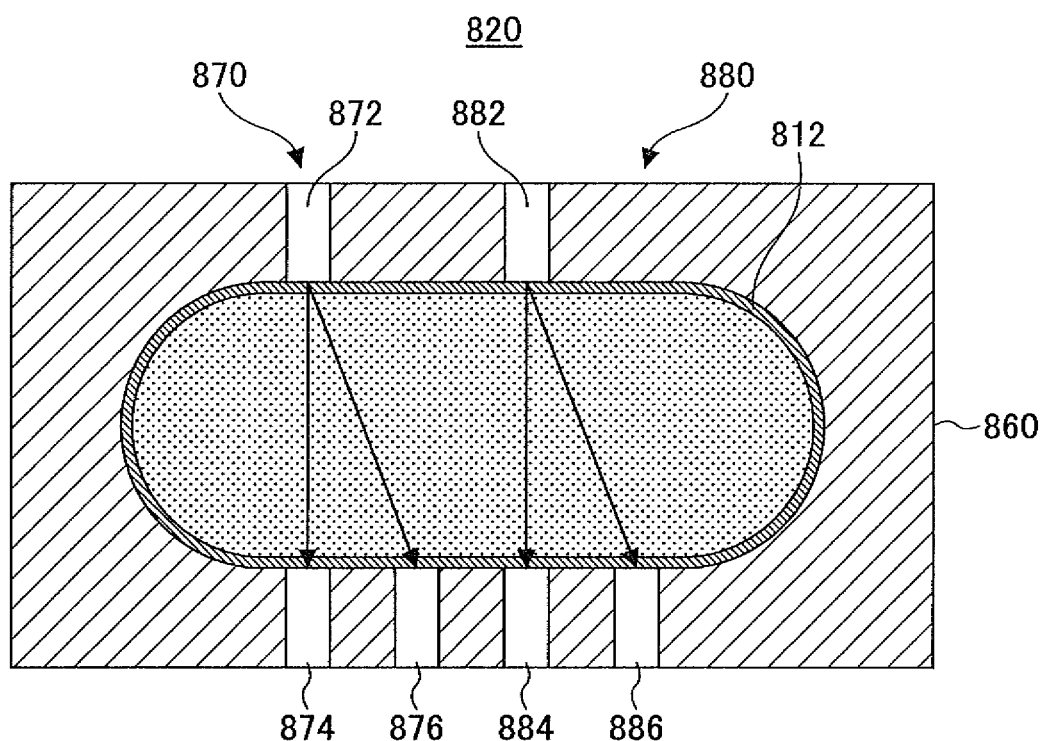
FIG. 16 illustrates a schematic configuration diagram showing a longitudinal cross-section of a sensor unit 820 of embodiment 2.

FIG. 16 is a longitudinal schematic diagram showing a configuration of the sensor unit 820 of embodiment 2. As shown in FIG. 16, the sensor unit 820 includes a holding member 860 which holds a part of the dialysis tube 812 so as to be pressurized from an upper side and a lower side, and two sets of sensor parts 870 and 880. The first sensor part 870 includes a first light emitting part 872 arranged above the dialysis tube 812 and first and second light receiving parts 874 and 876 arranged below the dialysis tube 812. The second sensor part 880 includes, in a manner similar to the first sensor part 870, a second light emitting part 882 arranged above the dialysis tube 812 and third and fourth light receiving parts 884 and 886 arranged below the dialysis tube 812.

In this embodiment, the red blood cell concentration Rpw is measured by the two-point-two-wavelengths measuring method by using arithmetic expression (3). That is, by emitting laser lights with different wavelengths $\lambda 1$ and $\lambda 2$ (in this embodiment, $\lambda 1=805$ nm and $\lambda 2=680$ nm) from the first and second light emitting parts 872 and 882, the red blood cell concentration is measured as a function of only a hematocrit (Ht). Therefore, according to this calculation method, the red blood cell concentration can be accurately measured as a measurement value responsive to the hematocrit (Ht).

Embodiment 3

Figure 17:
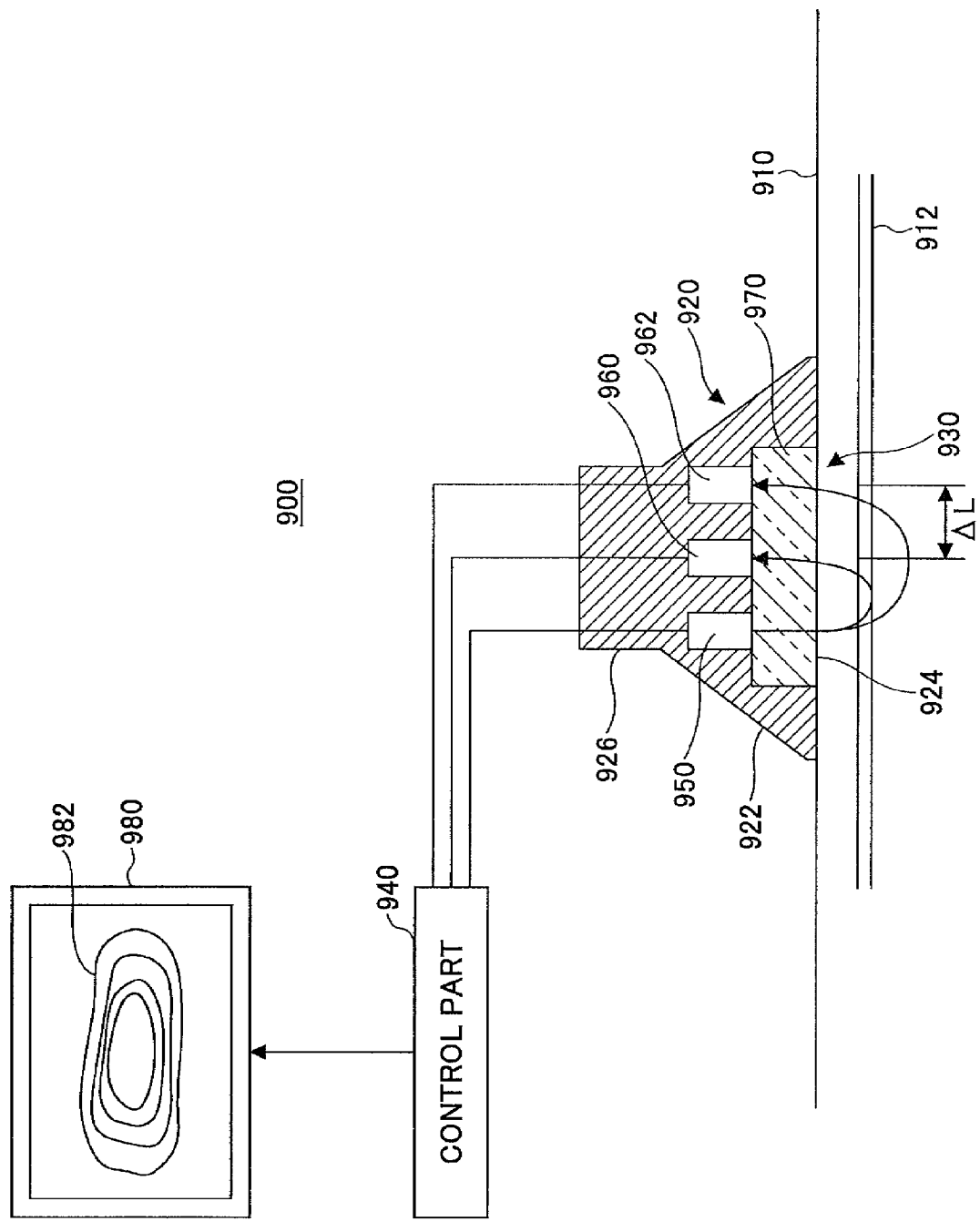
FIG. 17 illustrates a schematic diagram showing a configuration of a blood flow measuring apparatus of embodiment 3.

FIG. 17 is a schematic diagram showing a configuration of a blood flow measuring apparatus 900 of embodiment 3. As shown in FIG. 17, the blood flow measuring apparatus 900 of embodiment 3 includes a measuring part 920 which contacts a skin surface 910 of a measurement area, a sensor unit 930 incorporated in the measuring part 920, and a control part 940 which generates a blood flow measurement image according to the measurement data outputted by the sensor unit 930.

The measuring part 920 is formed in such a size that can be carried by hand. For example, the measuring part 920 can be moved as required depending on a part of a human body where a blood flow is measured. Further, the measuring part 920 has a cone-shaped part 922 of which bottom surface serves as a measurement surface 924 to be in contact with the measurement area. A holding part 926 protrudes on an upper part of the cone-shaped part 922. Therefore, a measurer can measure a blood flow of the measurement area by holding the holding part 926 and making contact with the measurement surface 924 on the skin surface 910 of the measured area as required.

The sensor unit 930 includes a light emitting part 950 which emits the laser light A, a pair of light receiving parts 960 and 962 arranged with different distances from a light emitting point, and an optical path separating member 970 formed of a hologram. The light emitting part 950 and the pair of light receiving parts 960 and 962 are mounted on an upper surface of the optical path separating member 970. A bottom surface of the optical path separating member 970 serves as the measurement surface 924.

Therefore, when the laser light A is emitted by the light emitting part 950 through the optical path separating member 970 onto the skin surface 910 of an arbitrary measurement area, the laser light A transmits through a blood flow in the blood vessel 912 present below the skin surface 910 and propagates to the measurement surface 924. The light receiving parts 960 and 962 individually receive the light which has propagated through the optical path separating member 970 and output electrical signals responsive to the amount of transmitted and received light to the control part 940.

In this embodiment, the red blood cell concentration Rp of blood flowing through the blood vessel 912 is measured by the two-point-one-wavelength measuring method by using arithmetic expression (2). That is, the red blood cell concentration is a function of a distance $\Delta L$ between the two light receiving parts 960 and 962 and the hematocrit (Ht). Therefore, since the distance $\Delta L$ between the two light receiving parts 960 and 962 is known in advance, the red blood cell concentration Rp is measured as a value having the hematocrit (Ht) as a coefficient. Therefore, by this calculation method, the red blood cell concentration can be accurately measured as a measurement value responsive to the hematocrit (Ht).

The control part 940 is connected to a monitor 980. The control part 940 generates image data from the measurement data of the blood flow measured by the sensor unit 930 of the measuring part 920, and displays a measurement image 9B2 based on the image data on the monitor 980. Accordingly, a measurer can check whether his/her blood flow is normal by holding the measuring part 920 in hand and making contact with the measurement surface 924 on the skin surface 910 while seeing the measurement image 982 displayed on the monitor 980.

The measuring part 920 of the blood flow measuring apparatus 900 can be moved as required. Therefore, blood flows of parts other than the head of a human body can be easily measured. Moreover, since the blood flow measuring apparatus 900 is highly portable, it can be used in any place in addition to a clinic of a medical institution (for example, in a temporary clinic, buildings other than medical institutions, a tent, or outdoors in a disaster area).

According to at least one embodiment, light emitted from a light emitting part is received by two or more light receiving parts arranged at positions with different distances from the light emitting part, and a blood flow state of a measurement area is measured according to signals obtained by the two or more light receiving parts. Therefore, a component depending on the oxygen saturation, which is included in the obtained signals, can be cancelled. As a result, blood flow and a brain activity state can be accurately measured according to a signal responsive to a proportion of a volume of red blood cells included in blood flowing through the measurement area.

This patent application is based on Japanese Priority Patent Application No. 2008-033617 filed on Feb. 14, 2008, the entire contents of which are hereby incorporated herein by reference.

What is claimed is:

1. A blood flow measuring apparatus comprising:
a plurality of sensor units, each of the plurality of sensor units including a light emitting part configured to emit first light and second light onto a measurement area, a light receiving part configured to receive the first light and second light transmitted through the measurement area, and a brain wave measuring electrode configured to measure a brain wave and integrally formed on a peripheral surface of the light emitting part and the light receiving part, a wavelength of the first light being different from a wavelength of the second light, wherein the plurality of sensor units are provided at different positions from each other and have the identical configuration to each other;
at least one more light receiving part configured to receive the first light and second light transmitted through the measurement area, wherein said at least one more light receiving part functions as a light receiving part of a different sensor unit from the sensor unit including the at least one more light receiving part among the plurality of sensor units; and
a control part configured to measure a blood flow state of the measurement area according to signals outputted by the light receiving parts
wherein the first light and second light emitted by the light emitting part is received by the light receiving parts arranged at different distances from the light emitting part and the light receiving parts output the signals responsive to the received first light and second light, and wherein the control part is configured to make a light emitting part of one of the plurality of sensor units emit the first light and the second light, detect amounts of transmitted light of the first and second light received by light receiving parts of at least two of the plurality of sensor units that are separated at different distances from the one of the plurality of sensor units, and is configured to measure the brain activity state of the measurement area according to measurement data responsive to the amounts of the transmitted light of the first light and the second light, said measurement data being outputted by the light receiving parts of the at least two of the plurality of sensor units, and
the control part is configured to measure the blood flow state of the measurement area by performing an arithmetic process to cancel a component of oxygen saturation in the blood, and execute the arithmetic process to calculate a test subject's red blood cell concentration as a function of only a hematocrit by ratioing between a red blood cell concentration in the first light and a red blood cell concentration in the second light,
wherein each of the plurality of sensor units includes an optical path separating member configured to have different refraction indexes with respect to light that proceeds from the light emitting part to the measurement area and light that proceeds from the measurement area to the light receiving part that is included it the sensor unit; and the light emitting part emits the light and said light receiving part included in the sensor unit receives the light through the optical path separating member.

2. The blood flow measuring apparatus as claimed in claim 1, wherein the first light has a wavelength that is less influenced in an optical characteristic by the oxygen saturation in the blood than a wavelength of the second light.

3. The blood flow measuring apparatus as claimed in claim 2, wherein the control part compares first amounts of transmitted light of the first light received by the light receiving parts and second amounts of transmitted light of the second light received by the light receiving parts to measure the blood flow state of the measurement area.

4. The blood flow measuring apparatus as claimed in claim 3, wherein the control part measures the blood flow state of the measurement area according to measurement data responsive to the first and second amounts of the transmitted light, said measurement data being outputted by light receiving parts.

5. The blood flow measuring apparatus as claimed in claim 1, wherein the brain wave measuring electrode includes a contact terminal at the end thereof.

6. The blood flow measuring apparatus as claimed in claim 1, wherein the brain wave measuring electrode is formed of indium tin oxide.

7. A brain activity measuring apparatus comprising:
a blood flow measuring apparatus configured to measure a blood flow of a brain; and
a control part configured to measure an activity state of the brain according to a result of the measurement preformed by the blood flow measuring apparatus,
wherein the blood flow measuring apparatus comprises:
a plurality of sensor units, each of the plurality of sensor units including a light emitting part configured to emit first light and second light onto a measurement area and a light receiving part configured to receive the first light and second light transmitted through the measurement area, and a brain wave measuring electrode configured to measure a brain wave and integrally formed on a peripheral surface of the light emitting part and the light receiving part, a wavelength of the first light being different from a wavelength of the second light, wherein the plurality of sensor units are provided at different positions from each other and have the identical configuration to each other; and at least one more light receiving part configured to receive the first light and second light transmitted through the measurement area, wherein the light emitted by the light emitting part is received by the light receiving parts arranged at different distances from the light emitting part and the light receiving part output signals responsive to the received light, and wherein said at least one more light receiving part functions as a light receiving part of a different sensor unit from the sensor unit including the at least one more light receiving part among the plurality of sensor units; and the control part is configured to measure a blood flow state of the measurement area by performing an arithmetic process to cancel a component of oxygen saturation in the blood, and execute the arithmetic process to calculate a test subject's red blood cell concentration as a function of only a hematocrit by ratioing between a red blood cell concentration in the first light and a red blood cell concentration in the second light, wherein the control part is configured to make a light emitting part of one of the plurality of sensor units emit the first light and the second light, detect amounts of transmitted light of the first and second light received by light receiving parts of at least two of the plurality of sensor units that are separated at different distances from the one of the plurality of sensor units, and measure the brain activity state of the measurement area according to measurement data responsive to the amounts of the transmitted light of the first light and the second light, said measurement data being outputted by the light receiving parts of the at least two of the plurality of sensor units, wherein each of the plurality of sensor units includes an optical path separating member configured to have different refraction indexes with respect to light that proceeds from the light emitting part to the measurement area and light that proceeds from the measurement area to the light receiving part that is included in the sensor unit; and the light emitting part emits the light and said light receiving part included in the sensor unit receives the light through the optical path separating member.

8. The brain activity measuring apparatus as claimed in claim 7, wherein the first light has a wavelength that is less influenced in an optical characteristic by the oxygen saturation in the blood than a wavelength of the second light.

9. The brain activity measuring apparatus as claimed in claim 7, wherein the control part sequentially makes the light emitting parts of all the sensor units emit the first light and the second light, detects an intensity of the light received by light receiving parts of at least two sensor units which are separated at different distances from the sensor unit which emits light, and measures the brain activity state of the measurement area according to measurement data responsive to the amounts of transmitted light of the first light and the second light, said measurement data being outputted by the said light receiving parts of the at least two sensor units.

10. The brain activity measuring apparatus as claimed in claim 7, wherein the brain wave measuring electrode includes a contact terminal at the end thereof.

11. The brain activity measuring apparatus as claimed in claim 7, wherein the brain wave measuring electrode is formed of indium tin oxide.

* * * * *